United States Patent
Gho et al.

(10) Patent No.: US 11,135,528 B2
(45) Date of Patent: Oct. 5, 2021

(54) EXTRACELLULAR VESICLE ISOLATION METHOD USING METAL

(71) Applicant: ROSETTA EXOSOME, Seoul (KR)

(72) Inventors: Yong Song Gho, Pohang-si (KR); Chang Jin Lee, Daegu (KR); Hyun Taek Park, Pohang-si (KR)

(73) Assignee: Rosetta Exosome, Seoul (KR)

( * ) Notice: Subject to any disclaimer, the term of this patent is extended or adjusted under 35 U.S.C. 154(b) by 17 days.

(21) Appl. No.: 16/477,859

(22) PCT Filed: Jan. 15, 2018

(86) PCT No.: PCT/KR2018/000673
§ 371 (c)(1),
(2) Date: Jul. 12, 2019

(87) PCT Pub. No.: WO2018/131966
PCT Pub. Date: Jul. 19, 2018

(65) Prior Publication Data
US 2020/0122058 A1    Apr. 23, 2020

(30) Foreign Application Priority Data
Jan. 13, 2017   (KR) .......................... 10-2017-0006430

(51) Int. Cl.
*B01D 15/38*    (2006.01)
*B01D 15/42*    (2006.01)
(Continued)

(52) U.S. Cl.
CPC ....... *B01D 15/3828* (2013.01); *B01D 15/424* (2013.01); *B01J 20/3265* (2013.01);
(Continued)

(58) Field of Classification Search
CPC .............. B01J 20/3236; B01J 20/3265; B01D 15/3828; B01D 15/424; B01D 15/426;
(Continued)

(56) References Cited

U.S. PATENT DOCUMENTS 6,812,023 B1 *  11/2004  Lamparski  ........... C12N 5/0639
                                                            435/325
6,899,863 B1 *   5/2005  Dhellin  .................... B01J 41/20
                                                            424/1.21
(Continued)

FOREIGN PATENT DOCUMENTS

JP       2006502857 A    1/2006
JP       2016502862 A    2/2016
(Continued)

OTHER PUBLICATIONS

SAFC Biosciences, "Protein Purification Techniques, vol. 4. Metal-Chelate Affinity Chromatography," Technical Bulletin (2006), 2 pages. (Year: 2006).*

(Continued)

*Primary Examiner* — Katherine Zalasky McDonald
(74) *Attorney, Agent, or Firm* — Carter, DeLuca & Farrell LLP; George Likourezos, Esq.

(57) ABSTRACT

An extracellular vesicle isolation method using a metal, and a method for isolating extracellular vesicles from various samples using metal affinity are disclosed. An extracellular vesicle isolation method has the advantages of not requiring costly equipment, of being able to be applied without limits on sample quantity, and of being capable of efficiently isolating extracellular vesicles while preserving the shape or properties thereof. Moreover, the method can be combined with existing isolation methods to maximize the efficiency of extracellular vesicle isolation, and can be utilized in disease diagnosis, disease treatment, multi-omics research, (Continued)

and extracellular vesicle property research and the like using the isolated extracellular vesicles.

19 Claims, 29 Drawing Sheets

(51) Int. Cl.
  *B01J 20/32* (2006.01)
  *B01D 15/36* (2006.01)
  *B01D 15/34* (2006.01)
  *C12N 1/16* (2006.01)
  *C12N 1/20* (2006.01)
  *C12N 5/071* (2010.01)

(52) U.S. Cl.
  CPC .............. *C12N 1/16* (2013.01); *C12N 1/20* (2013.01); *C12N 5/0602* (2013.01); *B01D 15/34* (2013.01); *B01D 15/361* (2013.01); *B01D 15/3804* (2013.01); *C12N 2509/00* (2013.01)

(58) Field of Classification Search
  CPC ........ B01D 15/3804; C12N 1/16; C12N 1/20; C12N 5/0606; C12N 5/0696; C12N 2509/00
  See application file for complete search history.

(56) References Cited

U.S. PATENT DOCUMENTS

| | | | | |
|---|---|---|---|---|
| 7,354,750 | B2* | 4/2008 | Simpson | B01D 15/3828 435/174 |
| 10,465,183 | B2* | 11/2019 | Skog | C12N 15/1006 |
| 10,808,240 | B2* | 10/2020 | Stoll | C12N 15/11 |
| 2004/0185545 | A1 | 9/2004 | Simpson et al. | |
| 2014/0093880 | A1* | 4/2014 | Kim | C12Q 1/6886 435/6.12 |
| 2015/0353920 | A1* | 12/2015 | Enderle | C12Q 1/6806 536/25.41 |
| 2018/0120299 | A1* | 5/2018 | Nishibu | C12N 15/09 |

FOREIGN PATENT DOCUMENTS

| | | | | |
|---|---|---|---|---|
| WO | 2004036189 | A2 | 4/2004 | |
| WO | WO-2013082518 | A1* | 6/2013 | ............. B01D 15/20 |
| WO | 2014107571 | A1 | 7/2014 | |
| WO | WO-2016088689 | A1* | 6/2016 | ............. C07K 17/02 |

OTHER PUBLICATIONS

Notarangelo et al. Ultrasensitive detection of cancer biomarkers by nickel-based isolation of polydisperse extracellular vesicles from blood. EBioMedicine 43 (2019) 114-126. (Year: 2019).*
Millipore Sigma, "Immobilized Metal Chelate Affinity Chromatography (IMAC)," Extracted from Affinity Chromatography Principles and Methods, GE Healthcare, 2007, 4 pages. (Year: 2007).*
Gaberc-Porekar et al. Perspectives of immobilized-metal affinity chromatography. J. Biochem. Biophys. Methods 49 (2001) 335-360. (Year: 2001).*
Santiago et al. TIM-4 structures identify a Metal Ion-dependent Ligand Binding Site where phosphatidylserine binds. Immunity. Author manuscript; available in PMC Dec. 1, 2008., p. 1-19. (Year: 2008).*
Juan-Colás et al., The Mechanism of Vesicle Solubilization by the Detergent Sodium Dodecyl Sulfate. Langmuir 2020, 36, 11499-11507. (Year: 2020).*
International Search Report of corresponding PCT Application No. PCT/KR2018/000673—6 pages (May 8, 2018).
Alves et al., "Affinity purification of bacterial outer membrane vesicles (OMVs) utilizing a His-tag mutant", Research in Microbiology, vol. 168, No. 2—9 pages (Oct. 20, 2016).
Berkovsky et al., "Use of metal-chelate affinity chromatography and hydrophobic interaction chromatography for purification of placental protein 12", Journal of Chromatography B: Biomedical Sciences and Applications, vol. 656, No. 2—5 pages (1994).
Nakai et al., "A novel affinity-based method for the isolation of highly purified extracellular vesicles", Scientific Reports, vol. 6, 33935—12 pages (2016).
Wako Catalog, MagCapture™ Exosome Isolation Kit PS, Life Science—4 pages (Jan. 20, 2016).
Website, Seoulin Bioscience, "[Wako] MagCapture™ Exosome Isolation Kit PS", <htttp://www. seoulin. co .kr/shop/board/view. php ?PHPSESSID=f5f53 fal 8670 17 43 94c8e4 86 28d3dl8b&id= newtecil&subSpeech = Wako&no=884&PHPSESSID= f5f53fal8670174394c8 e48628d3d18b> in 2 pages (Jan. 20, 2016).
Japanese Office Action received from the Jpanese Patent Office corresponding to Japanese Patent Application No. 2019-559248, dated Sep. 15, 2020.
Gonzales P. A. et al., Phosphoproteomics of Human Urinary Exosomes., TheFASEBJournal, and vol. 22 Issue S1 (2008), https://doi.org/10.1096/fasebj.22.1_supplement.1158.24NAKAI W. et.al., Scientificreports, 6: 33935 [Epub Sep. 23, 2016]. (Abstract Only).
Wako, "MagCapture Exosome Isolation Kit PS", pp. 1-20.
Annonymous. Wako Intoduing MagCapture (TM) Exosome Isolat, p. 1.

* cited by examiner (a)

(b)

(a)

(b)

EXTRACELLULAR VESICLE ISOLATION METHOD USING METAL

TECHNICAL FIELD

The present invention relates to a method for isolating extracellular vesicles by using a metal, and more particularly, relates to a method for isolating extracellular vesicles from various samples using a metal affinity.

BACKGROUND ART

Extracellular vesicles are nano-sized vesicles naturally secreted by all living organisms or cells from humans to bacteria through a universal cellular mechanism. Extracellular vesicles derived from eukaryotic cells have been reported to be involved in the differentiation of erythrocytes, the regulation of immune responses, and the like, and play an important role in the progression, metastasis, angiogenesis, and the like of cancer particularly in the micro environment of cancer cells. Thus, the extracellular vesicles have been drawing much attention in their applicability as a diagnostic marker for various diseases including cancer.

It has been reported that extracellular vesicles secreted by prokaryotic cells contain the constituents of prokaryotic cells in a similar manner to the extracellular vesicles of eukaryotic cells, induce a systemic inflammation and an acute lung inflammation disease depending on the route of vesicles introduction into the human body. In case of skin, they may cause atopic dermatitis, which is one of the representative diseases of modern people, by inducing a chronic inflammatory response in a localized skin tissue. Further, as a correlation between the bacteria-derived extracellular vesicles and the onset of cancer in the human body has been noticed, the prokaryotic cell-derived extracellular vesicles have also been attracting a great deal of attention.

The most important function of the extracellular vesicles is that the extracellular vesicles play an important role in an intercellular information exchange mechanism. Accordingly, the constituting components of the extracellular vesicles have also attracted a great deal of attention in the basic research and medical fields.

The extracellular vesicles are biological nanoparticles secreted in vivo or in vitro from various cells. They are membrane-structured vesicles, which are present in body fluids such as blood, urine, saliva, and tears, include a lipid bilayer derived from cells, and have various sizes in a range of 20 to 10,000 nm.

Since the extracellular vesicles bind to other cells and tissues to serve as a transporter which delivers intracellular substances such as membrane components, proteins, and RNA, they include proteins, lipids, amino acids, RNAs, and the like of original cells (mother cells) from which the extracellular vesicles are secreted. They provide thus an important basis for understanding the physiological and pathological characteristics of the mother cells. In addition, as it has been known that nucleic acids, growth hormones, proteins, and the like as included in the extracellular vesicles are protected by phospholipids in the form of cell membranes, and thus may perform a more stable function than soluble growth factors and cytokines, the significance of the extracellular vesicles has been increasingly recognized, while it is expected that the extracellular vesicles can be utilized for various purposes including diagnosis and treatment of a disease by analyzing substances contained in the extracellular vesicles.

Since extracellular vesicles have a size at the nanometer level and numerous substances in addition to the extracellular vesicles are present in body fluids, cell culture solutions, and the like, it is important to isolate extracellular vesicles from samples such as body fluids and cell culture solutions for the analysis of extracellular vesicles, while the isolation of extracellular vesicles is the most critical technique in all fields utilizing the extracellular vesicles.

Examples of an existing technique for isolating the extracellular vesicles include ultra-centrifugation, size exclusion, immunoaffinity isolation, a method using a microfluidics chip, a method using a polymer, or the like, while the ultra-centrifugation is one of the most widely used method among them. However, when ultra-centrifugation is used for isolating the extracellular vesicles, it presents such limitations as excessive amount of labor and time required due to its complex steps, the necessity of heavy equipment, and a large amount of a sample required for its tasks. Thus, ultra-centrifugation is not suitable for a clinical diagnosis which requires a rapid result using a small amount of a sample and a therapeutic method in which a large amount of the extracellular vesicles is needed.

Size exclusion is usually used with ultra-centrifugation, and thus has an advantage in that the purity of extracellular vesicles may be increased, but has a limitation in that extracellular vesicles can be attached to a filter, leading to a low yield rate after isolation.

Immunoaffinity isolation is a method for isolating extracellular vesicles by attaching antibodies to the extracellular vesicles, and has an advantage of a significantly high specificity, while being problematic since it is not suitable for practical diagnosis and treatment due to extensive time and costs to produce antibodies.

Therefore, there is an urgent need for a technique which can efficiently isolate and purify as much of an available amount of extracellular vesicles as possible while intactly maintaining the structure and function of the extracellular vesicles.

Affinity chromatography is a method for isolating a desired substance from a biological mixture based on a specific interaction such as a receptor-ligand. In particular, immobilized metal affinity chromatography (IMAC) is a method for isolating a protein from an aqueous solution using an interaction between metal ions and proteins. It has been used for the purpose of isolating and purifying a recombinant protein or peptide containing histidine by using a property that histidine or cysteine usually binds to metal ions. However, a method for isolating extracellular vesicles using the affinity between metal ions and extracellular vesicles has not been reported yet.

Recently, various methods utilizing non-invasive liquid biopsy for disease diagnosis have been conducted. In addition, efforts have been made to discover a new disease diagnostic marker by utilizing biological tissues or extracellular vesicles in body fluids and to diagnose a disease using the same. The fundamental problem of these efforts lies in the isolation of extracellular vesicles from living tissues or body fluids, while it is almost impossible to purify the extracellular vesicles in a body fluid exhibiting a relatively limited amount and high complexity by conventional methods. Therefore, there is an urgent need for a new isolation method distinguishable from conventional extracellular vesicular isolation methods.

DISCLOSURE

Technical Problem

An object of the present invention is to provide a method for isolating extracellular vesicles, the method comprising steps of: (a) immobilizing chelate ligands onto a stationary phase; (b) adding metals to the stationary phase onto which the chelate ligands are immobilized; (c) washing off metal residues which are not immobilized onto the stationary phase; (d) injecting samples comprising extracellular vesicles into the washed stationary phase; (e) washing of sample residues to which the metals are not bound in the stationary phase; and (f) eluting metal-bound extracellular vesicles from the stationary phase.

Another object of the present invention is to provide a method for isolating extracellular vesicles, the method comprising steps of: (a) immobilizing chelate ligands onto a stationary phase; (b) mixing metals with samples comprising extracellular vesicles, thereby binding the metals to the extracellular vesicles; (c) adding the obtained metal and sample mixture to the stationary phase onto which the chelate ligands are immobilized; (d) washing off residues which are not immobilized onto the stationary phase; and (e) eluting metal-bound extracellular vesicles from the stationary phase.

Still another object of the present invention is to provide a method for isolating extracellular vesicles, the method comprising steps of: (a) immobilizing chelate ligands onto a stationary phase; (b) adding samples comprising extracellular vesicles and metals to the stationary phase onto which the chelate ligands are immobilized; (c) washing off residues which are not immobilized onto the stationary phase; and (d) eluting metal-bound extracellular vesicles from the stationary phase.

Technical Solution

The present invention has been made in an effort to solve the above-described problems, and provides a method for isolating extracellular vesicles using the affinity between metals and extracellular vesicles using an immobilized metal affinity chromatography (IMAC) method which has been usually used for existing protein isolation methods.

As used herein, "immobilized metal affinity chromatography (IMAC)" refers to a chromatography technique of purifying extracellular vesicles using the affinity of extracellular vesicles for metals. That is, when samples to be analyzed are allowed to flow through a chromatography column, only substances having affinity for metal ions immobilized on the column are adsorbed, while the remaining components pass through the column without being adsorbed. Subsequently, the adsorbed substances are then eluted and purified by changing environmental conditions such as pH or imidazole, histidine, ethylendiamine tetraacetate (EDTA), and salt concentration.

According to the embodiments of the present invention, when various samples comprising extracellular vesicles are allowed to pass through a metal affinity chromatography column, extracellular vesicles in the samples are adsorbed onto the column by the affinity between metal ions immobilized onto the column and the extracellular vesicles, while the remaining samples which is not adsorbed onto the column exit the column. In this way, the extracellular vesicles may be easily isolated from various samples without any physical and chemical deformation, and thus the isolated extracellular vesicles as such are easily applicable for diagnosis, treatment, multi-omics research, and extracellular vesicle property research and the like.

As used herein, the term "extracellular vesicles" collectively refers to biological nanoparticles derived from cells of archaea, prokarya, or eukarya, and may include exosomes, argosomes, dexosomes, ectosomes, exovesicles, oncosomes, prominosomes, prostasomes, tolerosomes, microparticles, microvesicles, nanovesicles, blebbing vesicles, budding vesicles, exosome-like vesicles, matrix vesicles membrane vesicles, shedding vesicles, membrane particles, shedding microvesicles, membrane blebs, epididimosomes, promininosomes, texosomes and archeosomes, but is not limited thereto.

The present invention provides a method for isolating extracellular vesicles, the method comprising steps of: (a) immobilizing chelate ligands onto a stationary phase; (b) adding metals to the stationary phase onto which the chelate ligands are immobilized; (c) washing off metal residues which are not immobilized onto the stationary phase; (d) injecting samples comprising extracellular vesicles into the washed stationary phase; (e) washing off sample residues to which the metals are not bound in the stationary phase; and (f) eluting metal-bound extracellular vesicles from the stationary phase.

Such a method for isolating extracellular vesicles according to the present invention is schematically illustrated in FIG. 1A.

Further, the present invention provides a method for isolating extracellular vesicles, the method comprising steps of: (a) immobilizing chelate ligands onto a stationary phase; (b) mixing metals with samples comprising extracellular vesicles, thereby binding the metals to the extracellular vesicles; (c) adding the obtained metal and sample mixture to the stationary phase onto which the chelate ligands are immobilized; (d) washing off residues which are not immobilized onto the stationary phase; and (e) eluting metal-bound extracellular vesicles from the stationary phase.

Such a method for isolating extracellular vesicles according to the present invention is schematically illustrated in FIG. 1B.

In addition, the present invention provides a method for isolating extracellular vesicles, the method comprising steps of: (a) immobilizing chelate ligands onto a stationary phase; (b) adding samples comprising extracellular vesicles and metals to the stationary phase onto which the chelate ligands are immobilized; (c) washing off residues which are not immobilized onto the stationary phase; and (d) eluting metal-bound extracellular vesicles from the stationary phase.

Such a method for isolating extracellular vesicles according to the present invention is schematically illustrated in FIG. 1C.

As used herein, the term "stationary phase" refers to a substrate for immobilizing one substance out of two substances exhibiting biologically high specific affinity in affinity chromatography. Specifically, the stationary phase according to the present invention may be one or more selected from the group consisting of an agarose bead, a sepharose bead, a magnetic bead, a gold nanoparticle, an iron oxide nanoparticle, a nylon membrane, a nitrocellulose membrane, a PVDF membrane, paper, plastic, sand, glass, and a metal sensor chip, but is not limited thereto.

As used herein, the term "chelate ligands" refers to an atomic group comprising two or more possible coordination atoms for forming a chelate complex with a metal, while being called a tridentate ligand, a tetradentate ligand, a pentadentate ligand, a hexadentate ligand, and the like according to the number of coordination atoms. The chelate ligands of the present invention may be one or more selected from the group consisting of iminodiacetic acid (IDA), nitrilotriacetic acid (NTA), tris-(carboxymethyl)ethylenediamine (TED), ethylenediamine, ethylenediamine tetraacetate (EDTA), alkylenediamine triacetic acid, diethylenetriaminepentaacetic acid (DTPA), ethylene glycol-bis(β-aminoethyl ether)-N,N,N',N'-tetraacetic acid (EGTA), phosphoserine, and 1,4,7-triazocyclononane (TACN), but is not limited thereto as long as the chelate ligands can immobilize a metal used in the present invention onto the stationary phase.

As used herein, the term "metals" refers to a metal which has a specific affinity for the extracellular vesicles and may bind to the extracellular vesicles in a sample. The metals may be preferably metal ions, and more preferably transition metal ions. The metals according to the present invention may be metals used in typical immobilized metal affinity chromatography (IMAC), such as aluminum (Al) and gallium (Ga) in addition to the transition metals, and are not limited thereto as long as the metals have a specific affinity for extracellular vesicles to be isolated.

The transition metals include elements from Periods 4 to 7 and Groups 3 to 12 in the Periodic Table of the Elements, and are characterized by being present in the form of a complex ion by forming an ion-bound compound with a non-metal. Specifically, the transition metals of the present invention may be one or more selected from the group consisting of scandium (Sc), yttrium (Y), titanium (Ti), zirconium (Zr), hafnium (Hf), rutherfordium (Rf), vanadium (V), niobium (Nb), tantalum (Ta), dubnium (Db), chromium (Cr), molybdenum (Mo), tungsten (W), seaborgium (Sg), manganese (Mn), technetium (Tc), rhenium (Re), bohrium (Bh), iron (Fe), ruthenium (Ru), osmium (Os), hassium (Hs), cobalt (Co), rhodium (Rh), iridium (Ir), meitnerium (Mt), nickel (Ni), palladium (Pd), platinum (Pt), darmstadtium (Ds), copper (Cu), silver (Ag), gold (Au), roentgenium (Rg), zinc (Zn), cadmium (Cd), mercury (Hg), and copernicium (Cn).

As used herein, the term "samples" includes biological samples, cell culture solutions, or tissue samples, and the like comprising the extracellular vesicles. Specifically, the samples may be one or more selected from the group consisting of a mammal cell culture medium, a bacteria cell culture medium, a yeast culture medium, a tissue extract, a cancer tissue, serum, blood plasma, saliva, tears, sweat, urine, feces, cerebrospinal fluid (CSF), ascites, amniotic fluid, semen, milk, dust, fresh water, seawater, soil, and fermented food for use as a sample, but are not limited thereto.

The extracellular vesicle isolation method of the present invention relates to a method for isolating metal-bound extracellular vesicles from the samples using a property that extracellular vesicles to be isolated specifically bind to metals. In the isolation method of the present invention, first, a stationary phase on which chelate ligands are immobilized is prepared. Ligand-metal chelate compounds are formed by adding metals and extracellular vesicle-containing samples to the stationary phase, and extracellular vesicles can be then isolated from the samples by forming a metal-extracellular vesicle bond.

The present invention provides three different methods in terms of adding the metals and the samples to the stationary phase onto which the chelate ligands are immobilized.

First, the method according to the present invention forms metal chelate compounds by adding the metals to the stationary phase onto which the chelate ligands are immobilized and washing off non-bound metals. Next, the samples comprising extracellular vesicles are added to the stationary phase on which the metal chelate compounds are formed and thereby the metals are bound to the extracellular vesicles. Then, target extracellular vesicles can be isolated from the samples by eluting remaining metal-bound extracellular vesicles from the stationary phase.

According to the present invention, a method of loading chelate ligands, metals, or samples to the stationary phase may include a gravity-type method, a pump-type method (liquid chromatography system), a syringe-type method, a rotation-type method, or a vacuum-type method, but is not limited thereto.

In order to bind chelate ligands, metals, or samples to the stationary phase or to wash off non-bound substances, it is possible to apply various conditions which those skilled in the art to which the present technique belongs may understand. Specifically, a pH of a buffer solution, a concentration of NaCl, and a concentration of imidazole and the like may be adjusted. Preferably, for the binding and washing conditions of the present invention, a buffer solution with a pH of 3 to 12, 0 to 2 M NaCl, 0 to 100 mM imidazole, or a combination of the conditions may be applied.

In order to elute the extracellular vesicles bound to the stationary phase according to the present invention, various conditions may be employed which those skilled in the art to which the present invention belongs may understand. Specifically, the extracellular vesicles may be eluted by adjusting a pH of a buffer solution, a concentration of NaCl, a concentration of imidazole, a concentration of a chelating agent, and the application of another chelating agent, but such elution method is not limited thereto. Preferably, for the elution conditions of the present invention, a buffer solution with a pH of 10 or less, 0 to 2 M NaCl, 0 to 2 M imidazole, a 0 to 2 M metal chelating agent, or a combination of the conditions may be applied.

A second method of the present invention comprises mixing a small amount of the metals with the samples before loading to the stationary phase onto which the chelate ligands are immobilized so as to bind the metals to the extracellular vesicles, and then adding the samples comprising the bound product to the stationary phase. Target extracellular vesicles may be isolated from the samples by binding metal-bound extracellular vesicles to the chelate ligands present on the stationary phase.

A third method of the present invention is directed to a method of simultaneously forming a chelate ligand-metal-extracellular vesicle bound product by simultaneously loading the metals and the samples to the stationary phase onto which the chelate ligands are immobilized. The extracellular vesicles may be isolated from the samples by washing and removing substances which are not bound to the stationary phase.

The extracellular vesicle isolation methods of the present invention may further include a step of pre-treating the samples before loading the sample onto the stationary phase.

Furthermore, the extracellular vesicle isolation methods of the present invention may further include a step of post-treating the extracellular vesicles isolated according to the methods of the present invention.

The pre-treatment step of the present invention is a partial purification step of the non-purified samples, and may be conducted by one or more methods selected from centrifugation, ultracentrifugation, filtration, ultrafiltration, sonication, density gradient ultracentrifugation, size-exclusion chromatography, ion exchange chromatography, affinity chromatography, polymer-based precipitation, or organic solvent precipitation, without being limited thereto.

The post-treatment step of the present invention is a purification step of the isolated extracellular vesicles, and may be conducted by one or more methods selected from centrifugation, ultracentrifugation, filtration, ultrafiltration, sonication, density gradient ultracentrifugation, size-exclusion chromatography, ion exchange chromatography, affinity chromatography, polymer-based precipitation, or organic solvent precipitation, without being limited thereto.

The present invention also provides extracellular vesicles isolated from the isolation methods as described above.

Advantageous Effects

The extracellular vesicle isolation methods according to the present invention have advantages of being capable of efficiently isolating the extracellular vesicles while preserving the shape or properties thereof because costly equipment such as a centrifuge is not required and the samples are not exposed to an extreme environment during the isolation process. Further, the method of the present invention can be applied in combination with existing isolation methods, and can maximize the efficiency of extracellular vesicle isolation by applying the method of the present invention before or after performing the existing methods.

In addition, the extracellular vesicle isolation method of the present invention can rapidly and effectively isolate extracellular vesicles without any limitation in the amount of sample, and thus can play an important role in mass production of extracellular vesicles, while being utilized for clinical diagnosis by applying the method of the present invention for pre-treating and post-treating a small amount of body fluid samples.

Furthermore, the extracellular vesicle isolation method of the present invention can fractionate the extracellular vesicles into their subsets using various metals based on the fact that the affinity of the extracellular vesicles for a specific metal varies depending on the types of the extracellular vesicles. The fractionated extracellular vesicle subsets can be utilized for multidimensional disease diagnosis, and can solve the problems of the existing diagnostic markers and enable various applications by applying the previously developed various disease diagnostic markers to the method of the present invention.

MODES OF THE INVENTION

Hereinafter, the present invention will be described in more detail through Examples. These Examples are only for exemplifying the embodiments of the present invention, and it will be apparent to those of ordinary skill in the art that the scope of the present invention is not interpreted to be limited to those Examples.

Example 1. Purification and Analysis of Sample Extracellular Vesicles 1-1. Isolation and Purification of Sample Extracellular Vesicles Remaining cells and precipitate were removed by centrifugation (repeated twice in total) of a freshly obtained culture solution of a colorectal cancer cell line SW480 at 500×g for 10 minutes. A precipitate was removed again by centrifugation (repeated twice in total) of the supernatant at 2,000×g for 20 minutes.

In order to perform the Pt purification and precipitation of extracellular vesicles, which is present in the supernatant, a solution for inducing precipitation of extracellular vesicles (8.4% polyethylene glycol 6000, 250 mM NaCl, 20 mM HEPES, and pH 7.4) was added to the supernatant and the resulting mixture was stored in a refrigerator for 16 hours, the precipitated extracellular vesicles were then harvested by centrifugation at 12,000×g for 30 minutes and dissolved in a HEPES-buffered saline (20 mM HEPES, 150 mM NaCl, and pH 7.4).

In order to perform the $2^{nd}$ purification of the extracellular vesicles using density and buoyancy, the sample was mixed with an OptiPrep (final concentration of 30%) and put the sample at the lowest layer of an ultracentrifuge container, and layers were then stacked in the order of 20% OptiPrep and 5% OptiPrep. OptiPrep buoyancy density gradient ultracentrifugation (30%, 20%, and 5% OptiPrep trilayers) was performed at 200,000×g for 2 hours. After ultracentrifugation, a density (1.08 to 1.12 g/ml) zone equal to extracellular vesicles was harvested.

Figure 2:
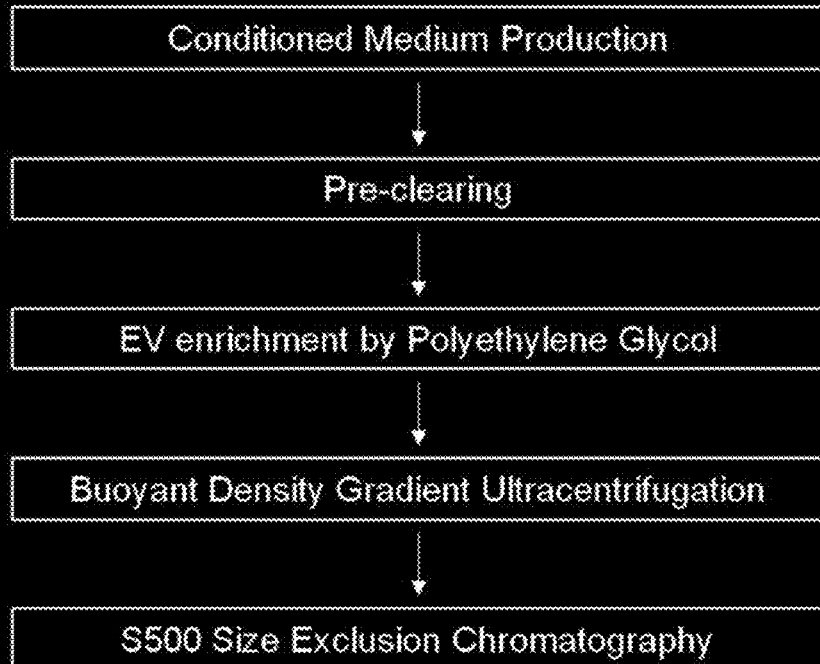
FIG. 2 is a conceptual diagram of a method for isolating sample extracellular vesicles from a colorectal cancer cell line SW480 according to an exemplary embodiment of the present invention.

In order to perform the $3^{rd}$ purification of the above purified extracellular vesicles, the purified extracellular vesicles were loaded onto a column (10×10 mm) filled with Sephacryl S500 using HPLC equipment, and an extracellular vesicle fraction finally purified by size chromatography was then harvested. The processes of isolating the 'sample extracellular vesicles' are illustrated in FIG. 2.

Figure 3:
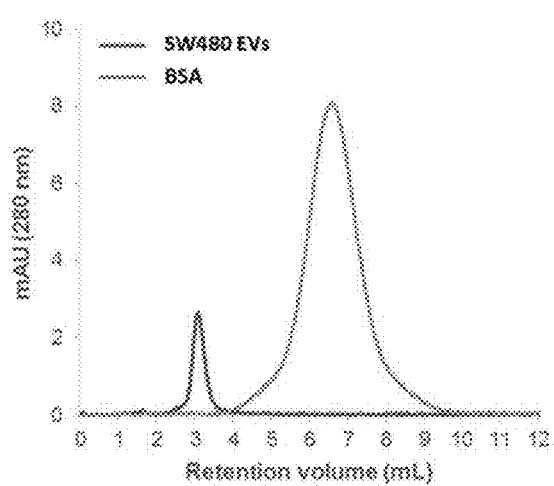
FIG. 3 is a result of confirming sample extracellular vesicles isolated according to an exemplary embodiment of the present invention by molecular size chromatography (a) and transmission electron microscopy (b).
Figure 3:
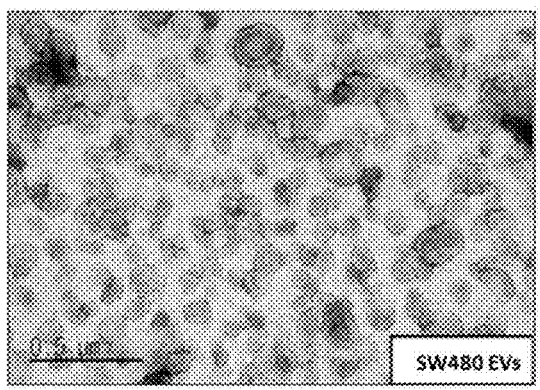

The extracellular vesicles which were purified from the colorectal cancer cell line SW480 as prepared by the above-mentioned method were checked by molecular size chromatography and an electron microscope. As illustrated in FIG. 3(A), a high purity of the extracellular vesicles derived from the colorectal cancer cell line purified by molecular size chromatography was confirmed, while as illustrated in FIG. 3(B), it was observed that the extracellular vesicles derived from the colorectal cancer cell line had a size of about 50 nm to about 200 nm using a transmission electron microscope.

1-2. Analysis of Purity of Sample Extracellular Vesicles

Figure 4:
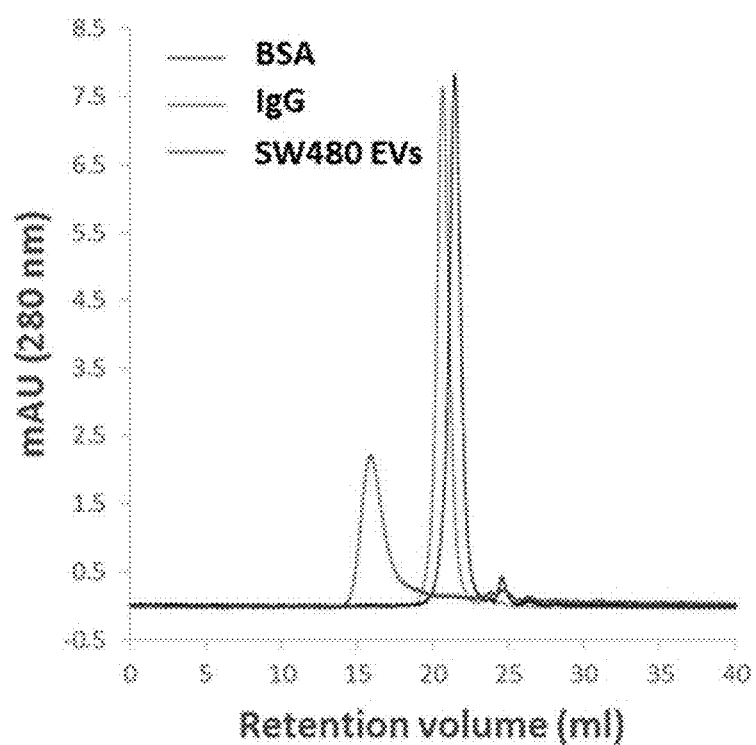
FIG. 4 is a chromatogram result for analyzing the purity of sample extracellular vesicles according to the present invention.

An HPLC system was used in order to verify the purity of the sample extracellular vesicles as purified from the colorectal cancer cell line SW480. After the sample extracellular vesicles purified by the above-mentioned method were loaded onto a TSKgel6000 gel for HPLC (7.5×600 mm), the purity of the purified sample was verified by tracking absorbance at 280 nm while flowing HEPES buffered saline as a mobile phase at 0.5 ml/min. As illustrated in FIG. 4, the sample extracellular vesicles (red) eluted at about 16 minutes exhibited a very high purity (>90%). This result showed that the sample extracellular vesicles were eluted more rapidly than albumin (BSA) (black: about 50 kDa) and an IgG antibody (blue: about 150 kDa), suggesting that the size of the sample extracellular vesicles is very large.

1-3. Analysis of Nanoparticles of Sample Extracellular Vesicle Fraction

In order to confirm and quantify nanoparticles, a nanoparticle tracking analysis was performed on the molecular size chromatography fraction of the sample extracellular vesicles using the HPLC equipment. A NanoSight LM10 device was used for the nanoparticle tracking analysis, while the sample extracellular vesicle fraction was tracked and recorded under the conditions of a camera level of 10 and a detection limitation of 5 for 60 seconds. The results are illustrated in FIG. 5.

Figure 5:
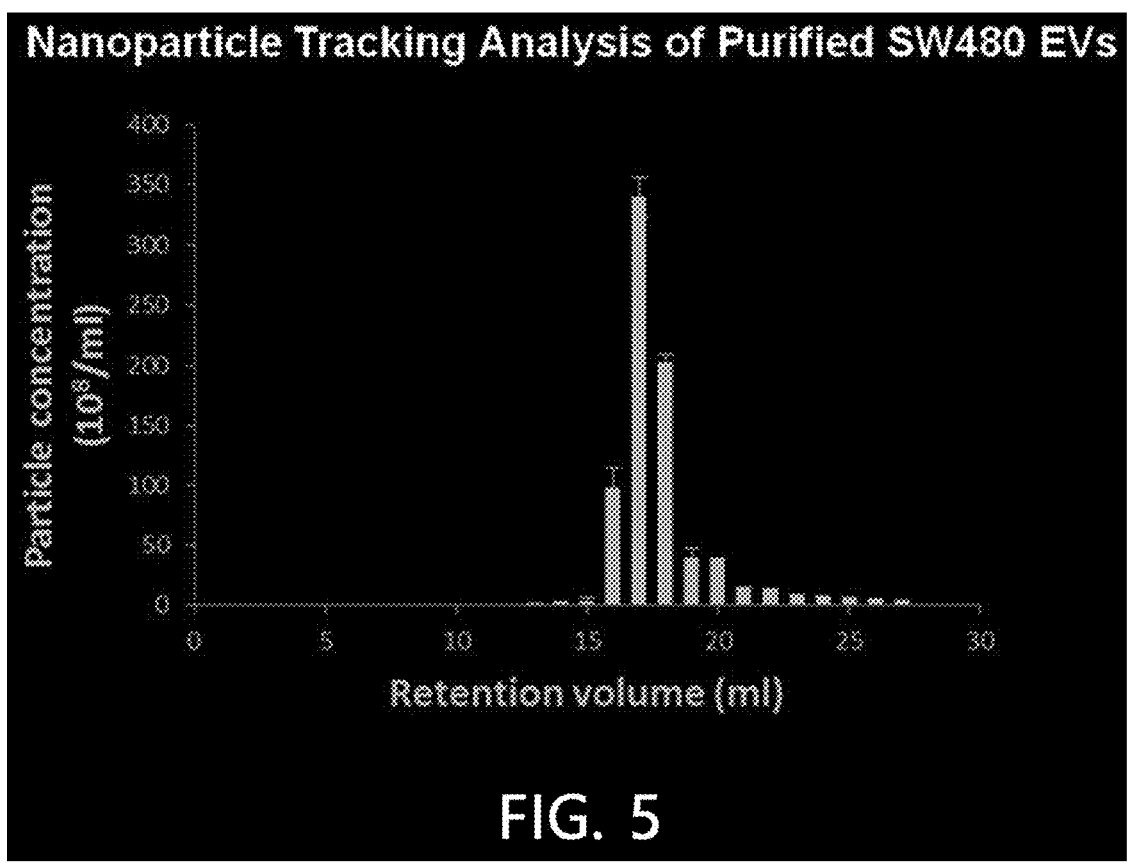
FIG. 5 is a result of analyzing nanoparticles of sample extracellular vesicles according to an exemplary embodiment of the present invention.

As illustrated in FIG. 5, it was confirmed that nanoparticles at a high concentration were present in the fraction eluted at 16 minutes among the molecular size chromatography fractions.

1-4. Sandwich ELISA Analysis of Sample Extracellular Vesicle Fraction

After the molecular size chromatography fractions of the sample extracellular vesicles were reacted with a microplate coated with polyclonal antibodies (rabbit polyclonal anti-SW480 EVs) specific for extracellular vesicles derived from a human colorectal cancer cell line, the bound extracellular vesicles were cultured with extracellular vesicle antibodies derived from a polyclonal anti-colorectal cancer cell line, which were bound to monoclonal anti-CD9 antibodies or biotin, and cultured with anti-mouse antibodies bound to horseradish peroxidase or streptavidin bound to horseradish peroxidase, and then the amount of extracellular vesicles was measured by measuring chemiluminescence.

Figure 6:
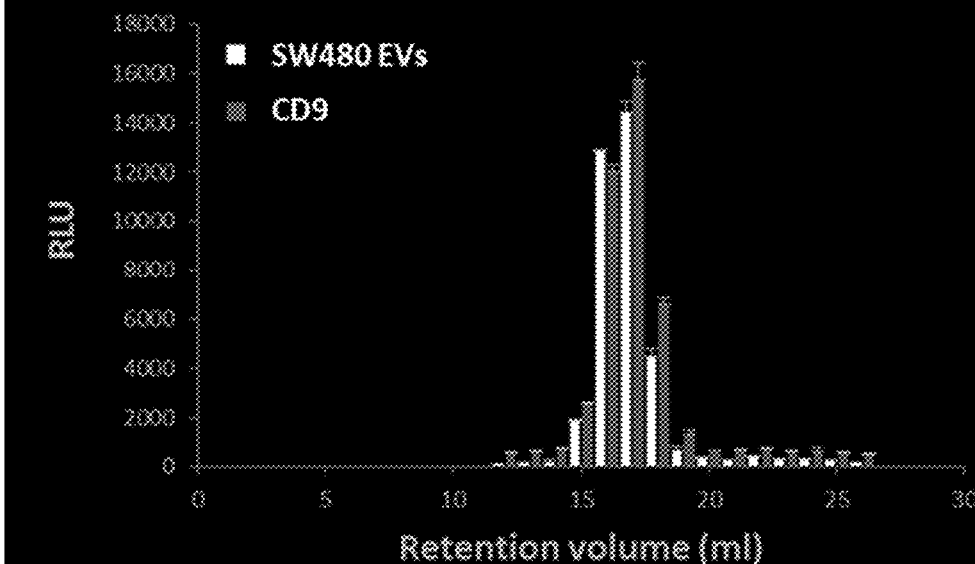
FIG. 6 is a sandwich ELISA result of analyzing nanoparticles of sample extracellular vesicles according to an exemplary embodiment of the present invention.

As a result, as illustrated in FIG. 6, it was found that the fraction eluted at 16 minutes among the molecular size chromatography fractions exhibited a high reactivity with monoclonal anti-CD9 antibodies along with extracellular vesicle antibodies derived from the polyclonal anti-colorectal cancer cell line.

Example 2. Binding Aspect of Sample Extracellular Vesicles to Stationary Phase in the Absence of Metal After sample extracellular vesicles ($4 \times 10^{10}$ particles) were loaded onto a column (1 ml) filled with a stationary phase (IDA-Sepharose) using HEPES buffer solution for 5 minutes using an HPLC system, they were washed with the same buffer solution for another 5 minutes. Then, chromatography was attained on column with concentration gradient at a pH of 7.2 using 0 to 500 mM imidazole/HEPES buffer solution for a 20 column volume, and eluates of all the processes including binding and washing processes were fractionated into 1-ml fractions, respectively.

Figure 7:
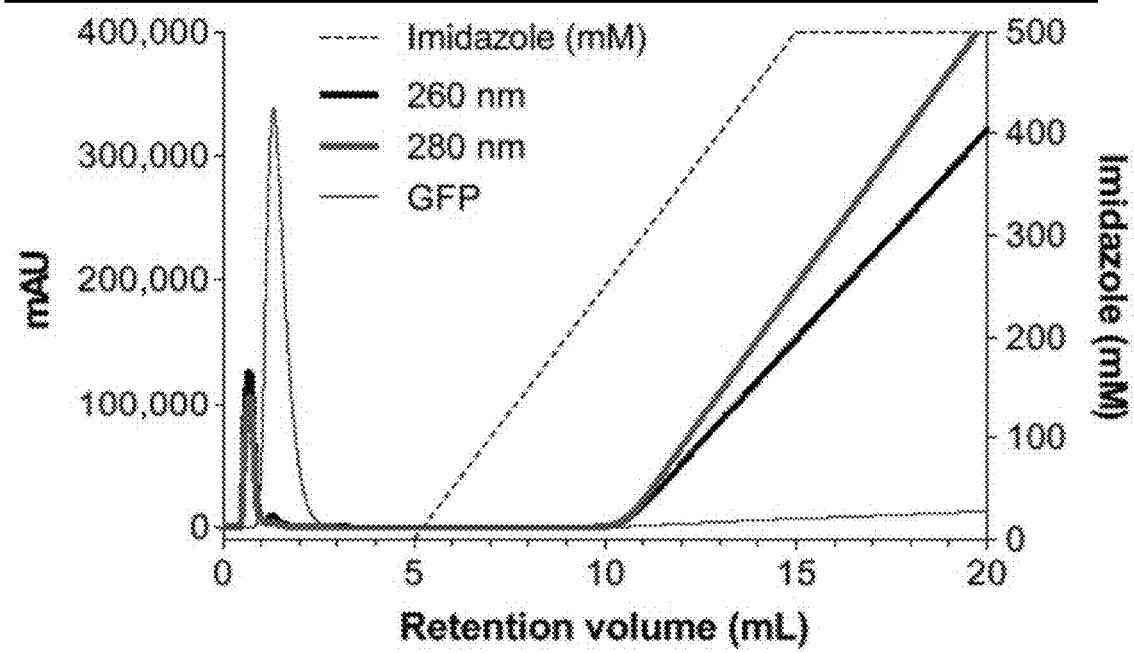
FIG. 7 is a chromatogram which analyzes a stationary phase binding aspect of sample extracellular vesicles when there is no metal according to an exemplary embodiment of the present invention.
Figure 8:
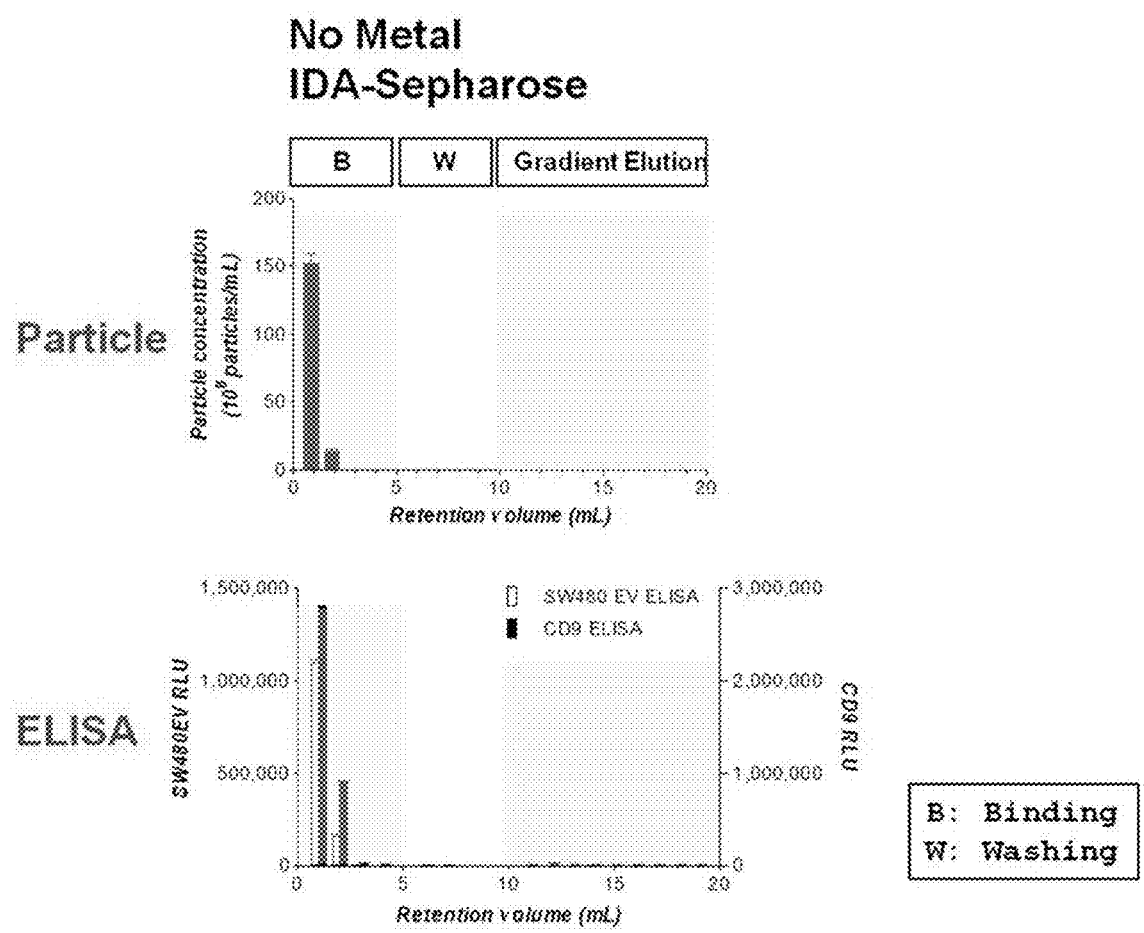
FIG. 8 is a result of analyzing a stationary phase binding aspect of sample extracellular vesicles when there is no metal according to an exemplary embodiment of the present invention.

A binding aspect of extracellular vesicles to the stationary phase was analyzed by performing a chromatogram analysis (absorbances at 260 nm and 280 nm were measured, respectively), a nanoparticle analysis, and sandwich ELISA on the fractionated eluate by the methods as described above, respectively. The results are illustrated in FIGS. 7 and 8. As seen from the results, it was observed that all the loaded sample extracellular vesicles were eluted without being bound to the stationary phase simultaneously at the time of their loading when no metal is present in the stationary phase.

Example 3. Analysis of Affinity of Sample Extracellular Vesicles for Cu(II)

After 0.5 ml of 500 mM Cu(II) ions were bound to a column (1 ml) filled with a stationary phase (IDA-Sepharose) using an HPLC system, non-bound residues were washed off with HEPES buffer solution of a 20 column volume.

Figure 9:
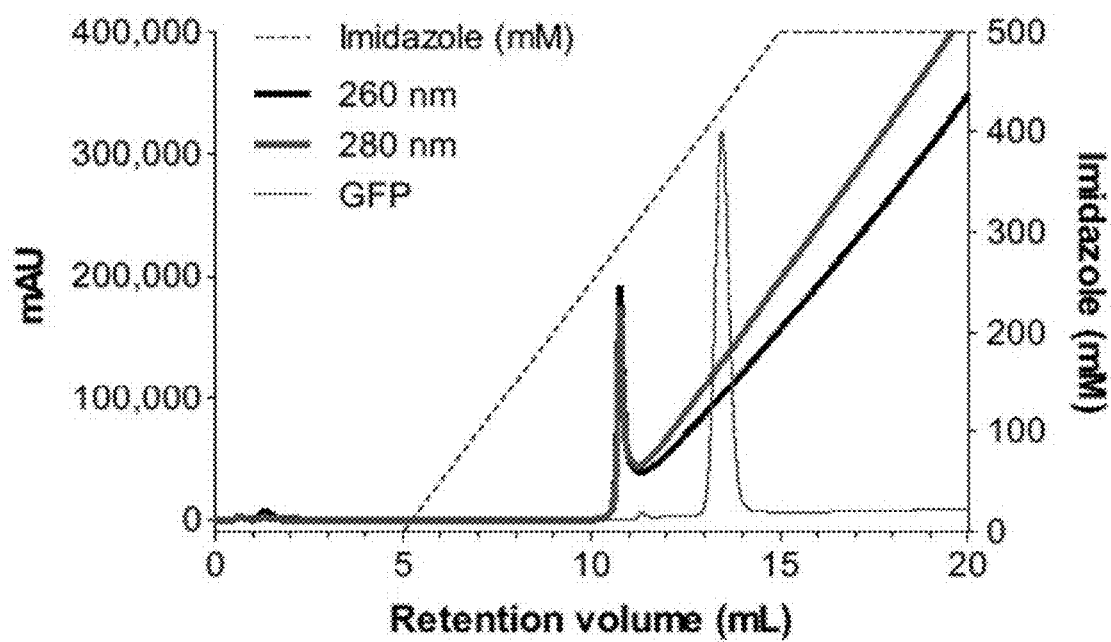
FIG. 9 is a chromatogram which analyzes the affinity of sample extracellular vesicles for Cu (II) according to an exemplary embodiment of the present invention.
Figure 10:
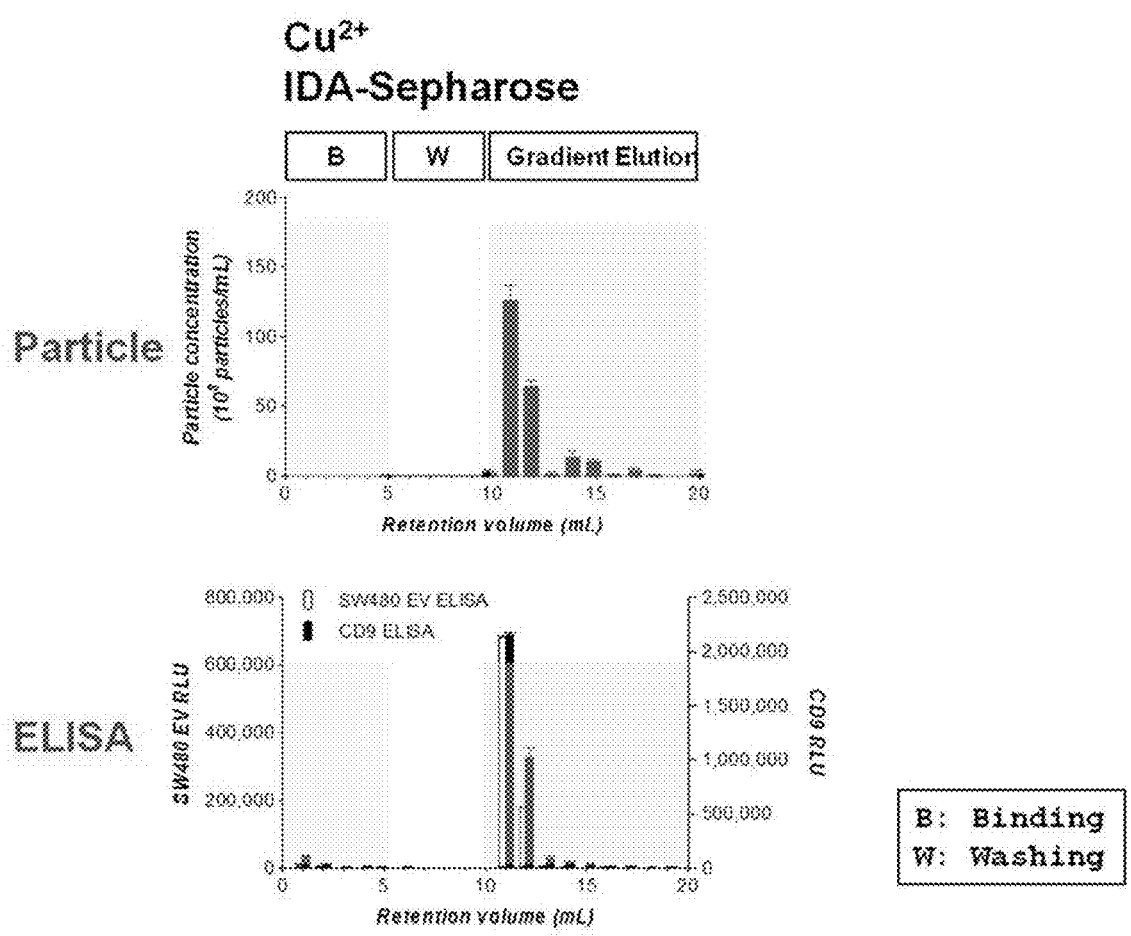
FIG. 10 is a result of analyzing the affinity of sample extracellular vesicles for Cu (II) according to an exemplary embodiment of the present invention.

After sample extracellular vesicles ($4\times10^{10}$ particles) were loaded onto the Cu(II) ions-bound stationary phase column using HEPES buffer solution for 5 minutes, the sample extracellular vesicles were washed with the same buffer solution for another 5 minutes. Eluates of all the processes including binding and washing processes were fractionated into 1-ml fractions, respectively, with a concentration gradient at a pH of 7.2 using 0 to 500 mM imidazole/HEPES buffer solution for a 20 column volume. A binding aspect of extracellular vesicles to the stationary phase was analyzed by performing a chromatogram analysis (absorbances at 260 nm and 280 nm were measured, respectively), a nanoparticle analysis, and sandwich ELISA on the fractionated eluate by the methods as described above. The results are illustrated in FIGS. 9 and 10. As a result, it was confirmed that all the sample extracellular vesicles were bound to the Cu(II) ions-bound stationary phase, while the sample extracellular vesicles were eluted as the concentration of imidazole was increased.

Example 4. Analysis of Affinity of Sample Extracellular Vesicles for Cu(I)

The affinity of the sample extracellular vesicles was analyzed in the same manner as in Example 3, except that Cu(I) ions were used as a metal to be added to the stationary phase (IDA-Sepharose).

Figure 11:
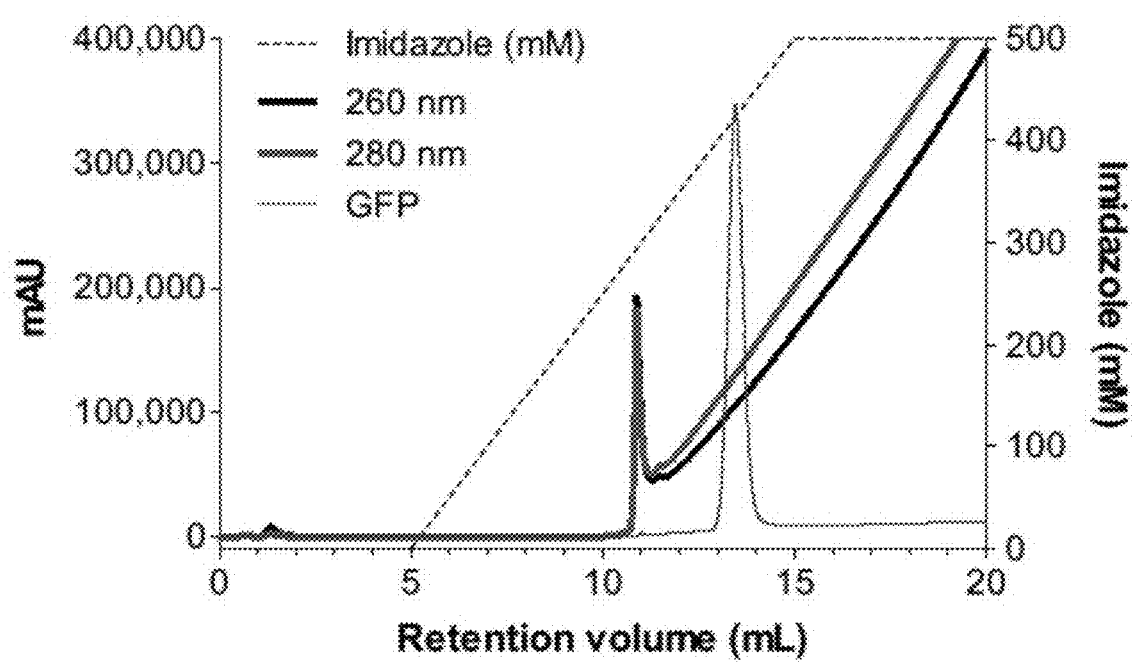
FIG. 11 is a chromatogram which analyzes the affinity of sample extracellular vesicles for Cu (I) according to an exemplary embodiment of the present invention.
Figure 12:
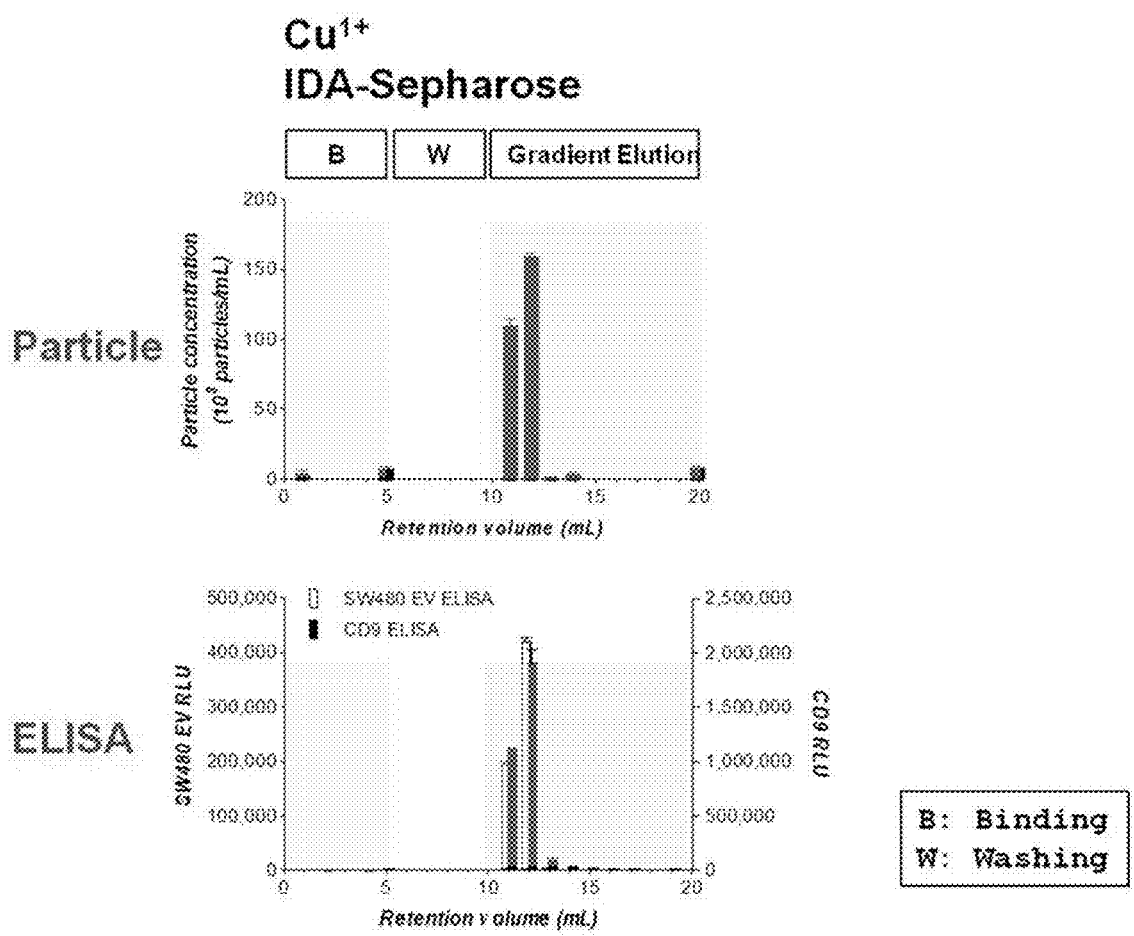
FIG. 12 is a result of analyzing the affinity of sample extracellular vesicles for Cu (I) according to an exemplary embodiment of the present invention.

As illustrated in FIGS. 11 and 12, it was found that all the sample extracellular vesicles were bound to the Cu(I) ions-bound stationary phase, while the sample extracellular vesicles were eluted as the concentration of imidazole was increased.

Example 5. Analysis of Sample Extracellular Vesicles for Zn(II)

After 0.5 ml of 500 mM Zn(II) ions were bound to a column (1 ml) filled with a stationary phase (IDA-Sepharose) using an HPLC system, non-bound residues were washed off with HEPES buffer solution of a 20 column volume.

Figure 13:
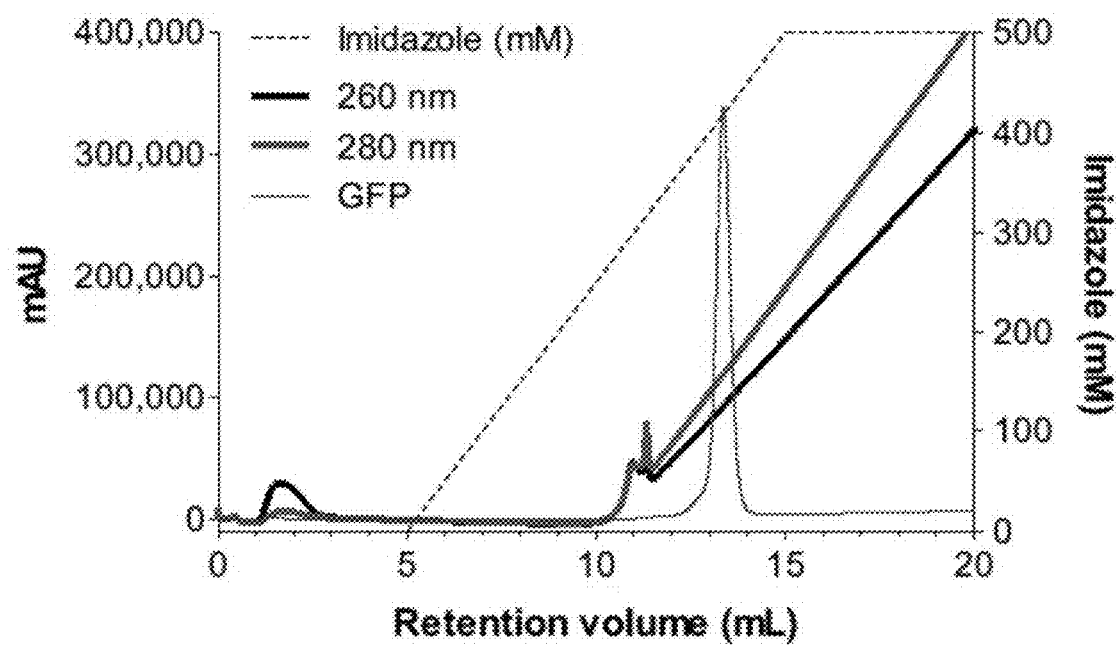
FIG. 13 is a chromatogram which analyzes the affinity of sample extracellular vesicles for Zn (II) according to an exemplary embodiment of the present invention.
Figure 14:
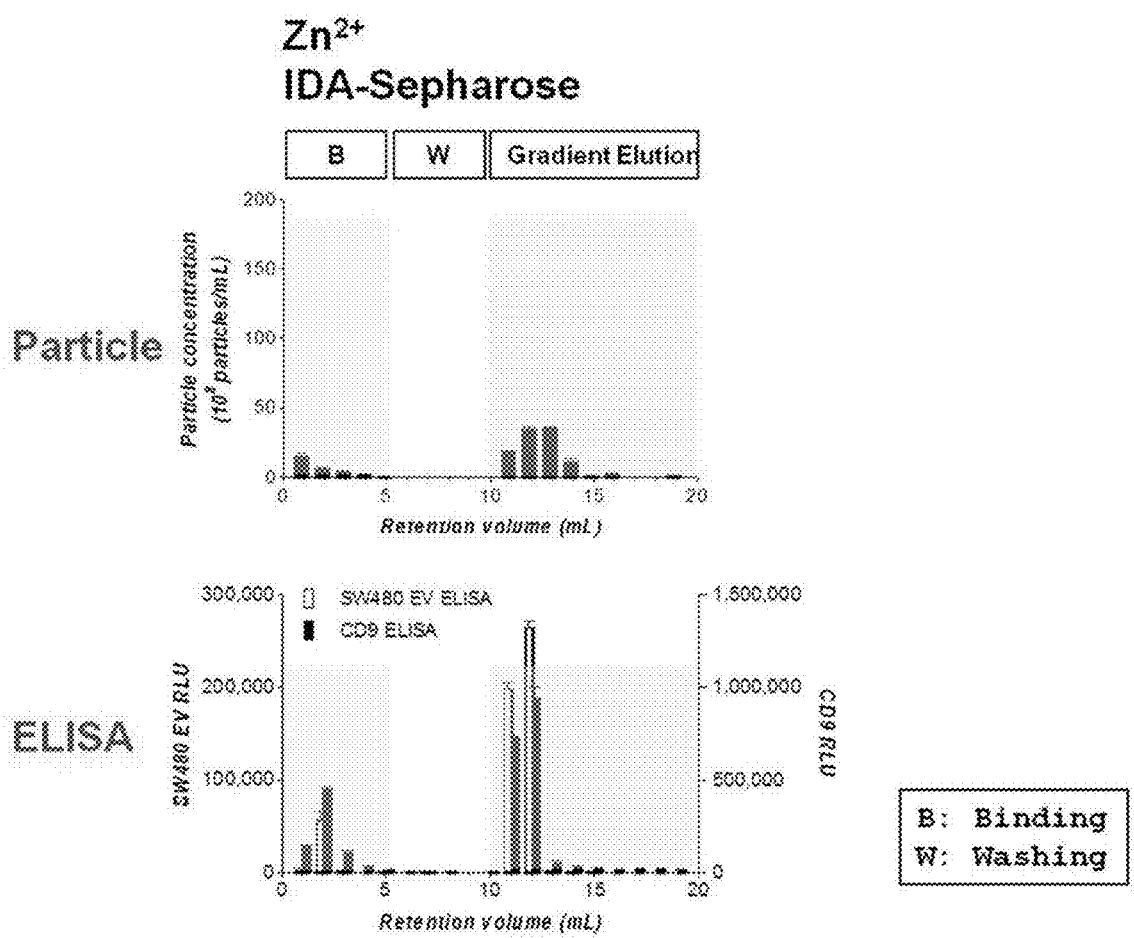
FIG. 14 is a result of analyzing the affinity of sample extracellular vesicles for Zn (II) according to an exemplary embodiment of the present invention.

After sample extracellular vesicles ($2\times10^{10}$ particles) were loaded onto the stationary phase column bound to Zn(II) ions using HEPES buffer solution for 5 minutes, the sample extracellular vesicles were washed with the same buffer solution for another 5 minutes, and eluates of all the processes including binding and washing processes were fractionated into 1-ml fractions, respectively, with a concentration gradient using 0 to 500 mM imidazole/HEPES buffer solution for a 20 column volume. A binding aspect of extracellular vesicles to the stationary phase was analyzed by performing a chromatogram analysis (absorbances at 260 nm and 280 nm were measured, respectively), a nanoparticle analysis, and sandwich ELISA on the fractionated eluate by the methods as described above. The results are illustrated in FIGS. 13 and 14.

As a result, it was confirmed that about 80% of the sample extracellular vesicles were bound to the Zn(II) ions-bound stationary phase, while the sample extracellular vesicles were eluted as the concentration of imidazole was increased. The remaining approximately 20% of the loaded sample extracellular vesicles were eluted simultaneously at the time of loading without being bound to the Zn(II) ions-bound stationary phase. This means that about 20% of the extracellular vesicles are a subset of the extracellular vesicles which does bind to Zn(II) ions and has a property distinguishable from that of the extracellular vesicles binding to the Zn(II) ions-bound stationary phase.

Example 6. Analysis of Affinity of Sample Extracellular Vesicles for Ni(II)

The affinity of the sample extracellular vesicles was analyzed in the same manner as in Example 3, except that Ni(II) ions were used as a metal to be added to the stationary phase (IDA-Sepharose).

Figure 15:
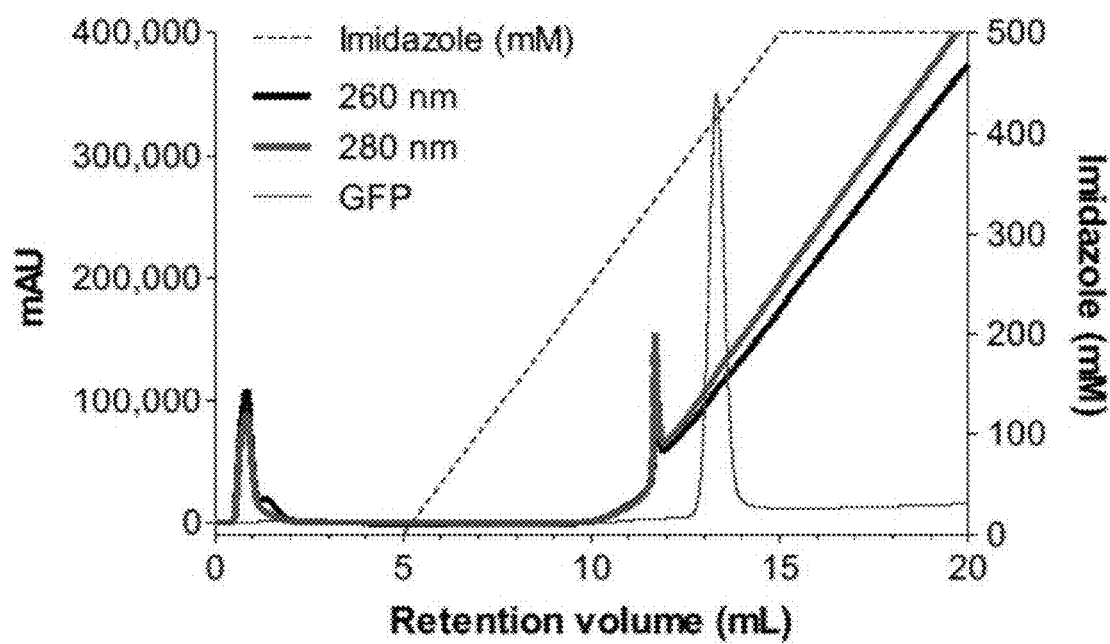
FIG. 15 is a chromatogram which analyzes the affinity of sample extracellular vesicles for Ni (II) according to an exemplary embodiment of the present invention.
Figure 16:
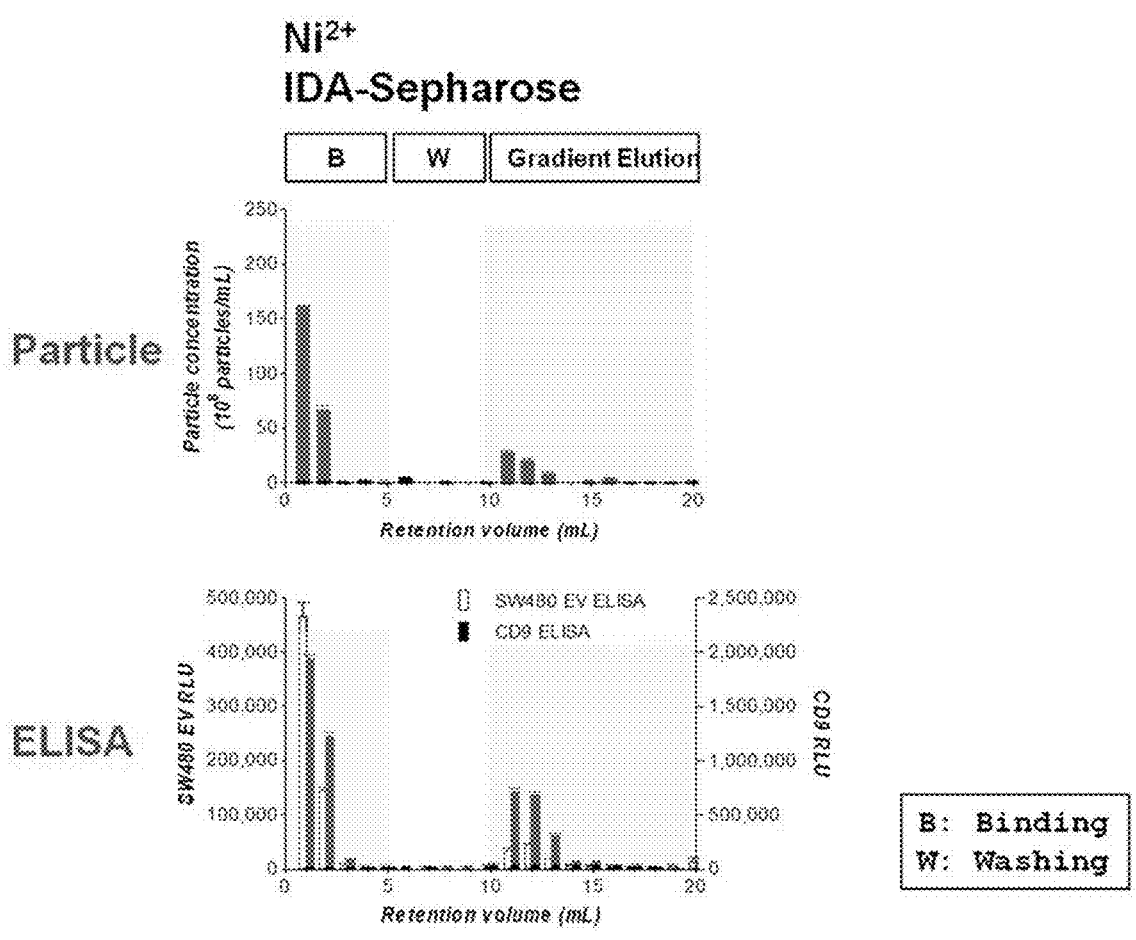
FIG. 16 is a result of analyzing the affinity of sample extracellular vesicles for Ni (II) according to an exemplary embodiment of the present invention.

As illustrated in FIGS. 15 and 16, it was confirmed that about 25% of the sample extracellular vesicles were bound to the Ni(II) ions-bound stationary phase, while the sample extracellular vesicles were eluted as the concentration of imidazole was increased. The remaining approximately 75% of the loaded sample extracellular vesicles were eluted simultaneously at the time of loading without being bound to the Ni(II) ions-bound stationary phase. This means that about 25% of the extracellular vesicle subset has a characteristic of binding to the Ni(II) ions-bound stationary phase.

Example 7. Analysis of Affinity of Sample Extracellular Vesicles for Co(II)

The affinity of the sample extracellular vesicles was analyzed in the same manner as in Example 3, except that Co(II) ions were used as a metal to be added to the stationary phase (IDA-Sepharose).

Figure 17:
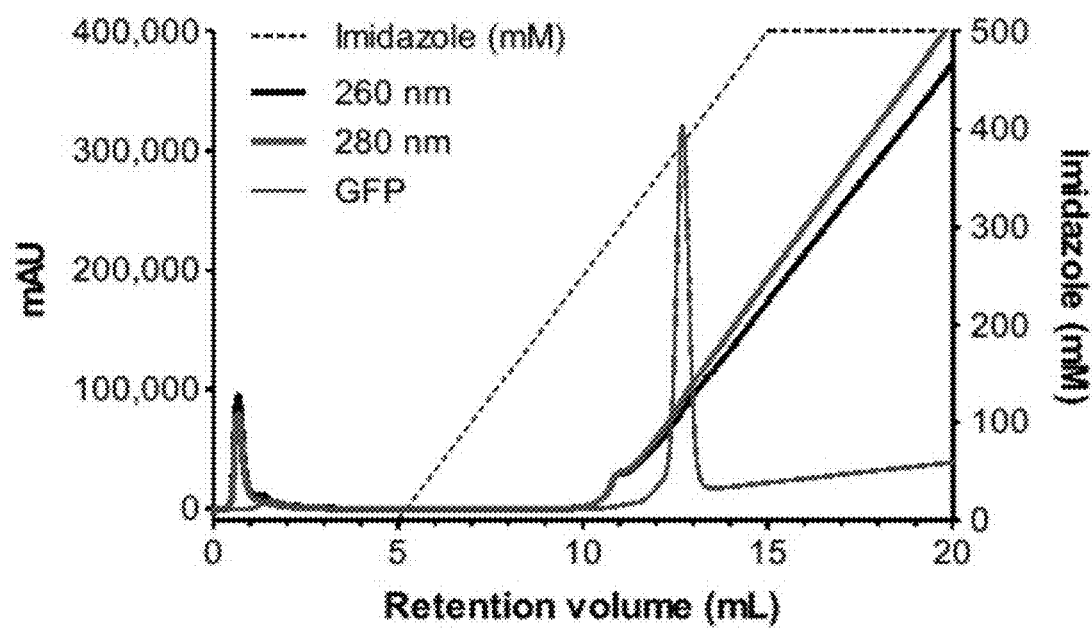
FIG. 17 is a chromatogram which analyzes the affinity of sample extracellular vesicles for Co (II) according to an exemplary embodiment of the present invention.
Figure 18:
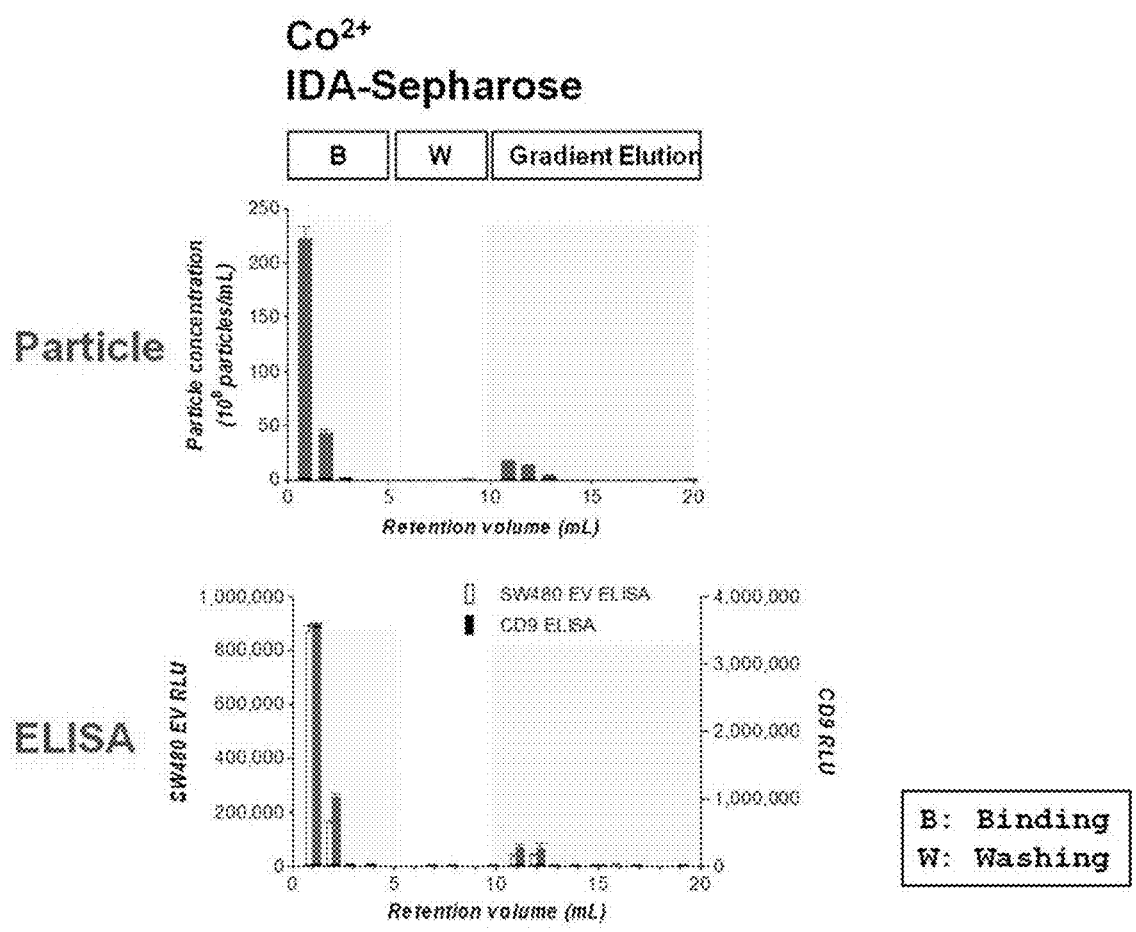
FIG. 18 is a result of analyzing the affinity of sample extracellular vesicles for Co (II) according to an exemplary embodiment of the present invention.

As illustrated in FIGS. 17 and 18, it was confirmed that about 10% of the sample extracellular vesicles were bound to the Co(II) ions-bound stationary phase, while the sample extracellular vesicles were eluted as the concentration of imidazole was increased. The remaining approximately 90% of the loaded sample extracellular vesicles were eluted simultaneously at the time of loading without being bound to the Co(II) ions-bound stationary phase. This means that about 10% of the extracellular vesicle subset has a characteristic of binding to the Co(II) ions-bound stationary phase.

Figure 1A:
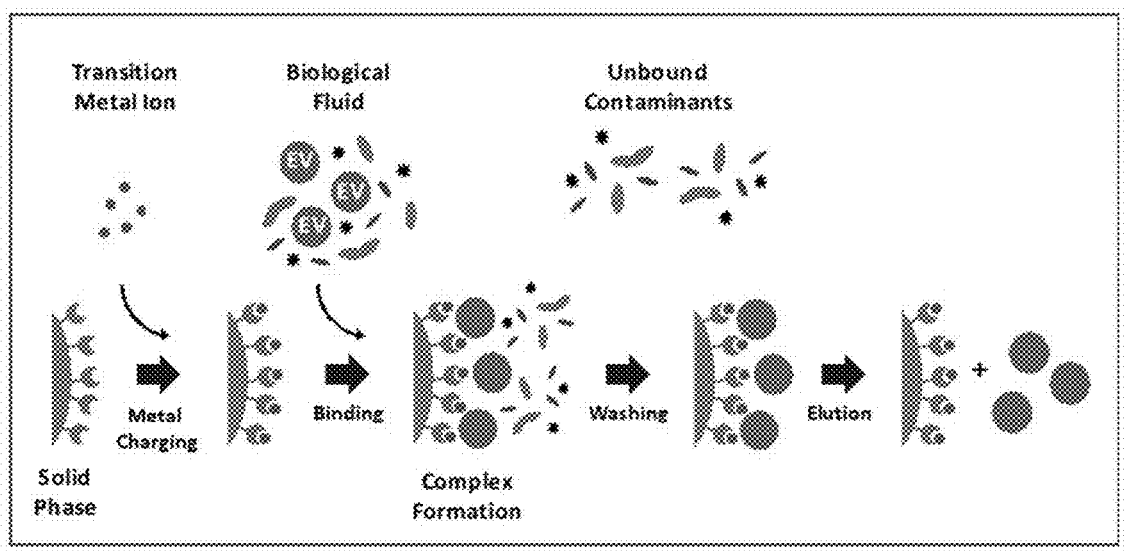
FIGS. 1A to 1C are schematic diagrams of the extracellular vesicle isolation methods according to the present invention.
Figure 1A:
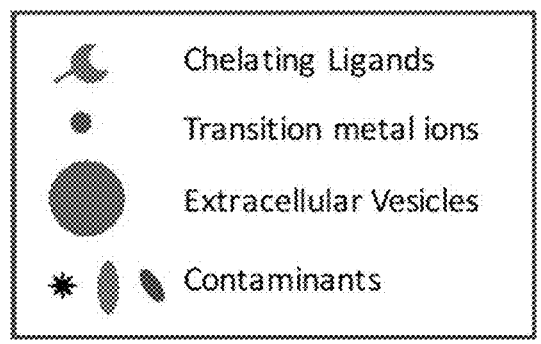

Example 8. Isolation of Extracellular Vesicles from Cell Culture Solution of Stem Cells (Crude Sample)—Pump Type Extracellular vesicles were isolated from a culture solution of stem cells using the first method (see FIG. 1A) among the methods for isolating extracellular vesicles according to the present invention. Specifically, after 0.5 ml of 500 mM Cu(II) ions were bound to a column (1 ml) filled with a stationary phase (IDA-Sepharose) using an HPLC system, non-bound residues were washed off with HEPES buffer solution of a 20 column volume.

5 ml of a culture solution (conditioned medium) of human mesenchymal cells (hMSC serum-free) which had not been pretreated was loaded onto the Cu(II) ions-bound stationary phase using HEPES buffer solution, followed by washing with the same buffer solution of a 5 column volume. The eluates were fractionated into 1-ml fractions through processes comprising binding and washing processes with a concentration gradient using 0 to 500 mM imidazole/HEPES buffer solution at 7.2 for a 20 column volume.

Chromatogram analysis (absorbance at 280 nm was measured) was performed on the fractionated eluates by the method as described above, and the same volume of the eluates were precipitated by trichloroacetic acid, followed by SDS-electrophoresis. Subsequently, signals for CD9, which is a typical marker for extracellular vesicles, were analyzed.

Figure 19:
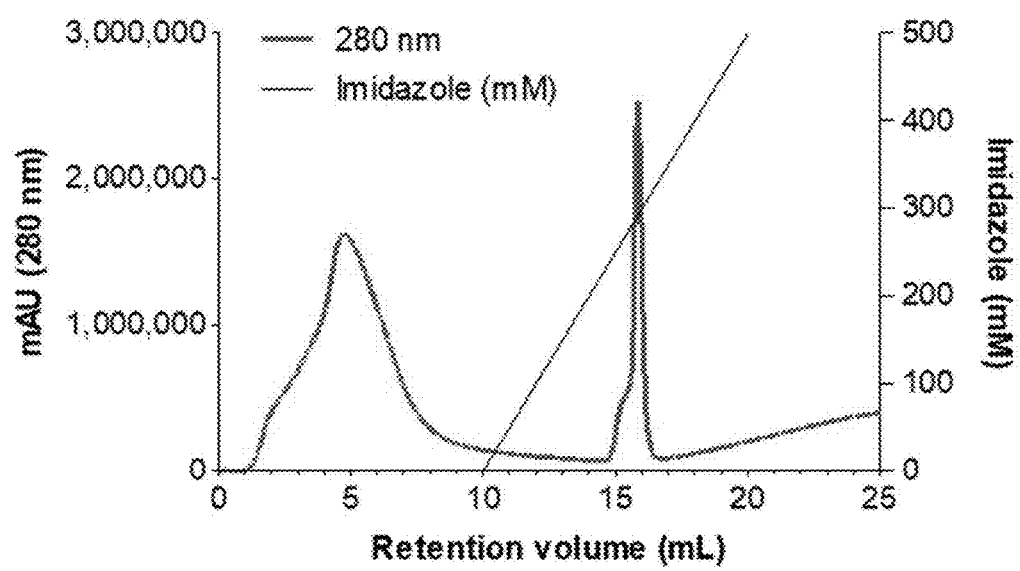
FIG. 19 is a result of confirming the result of isolating extracellular vesicles from a cell culture solution according to an exemplary embodiment of the present invention by a chromatogram (a) and a Western blot (b).
Figure 19:
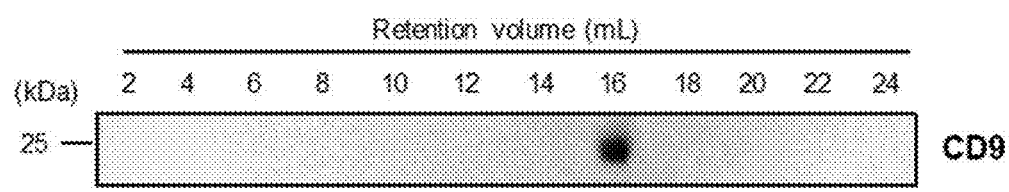

As illustrated in FIG. 19(A), the chromatogram results confirmed a signal for extracellular vesicles when the elution time was 16 minutes. As illustrated in FIG. 19(B), the western blot analysis results showed the detection of a strong CD9 signal from a fractionated product at the same elution time as that of the chromatogram results, confirming that the extracellular vesicles of the cell culture solution of human mesenchymal cells were bound to the Cu(II) ions-bound stationary phase, and thus were eluted and separated by an imidazole concentration gradient.

Example 9. Isolation of Extracellular Vesicles from Cell Culture Solution of Pre-Treated Colorectal Cancer Cell Line—Pump Type Extracellular vesicles were isolated from a culture solution of the colorectal cancer cell line using the first method (see FIG. 1A) among the methods for isolating extracellular vesicles according to the present invention. Specifically, after 0.5 ml of 500 mM Cu(II) ions were bound to a column (1 ml) filled with a stationary phase (IDA-Sepharose) using an HPLC system, non-bound residues were washed off with HEPES buffer solution of a 20 column volume.

Extracellular vesicles were precipitated by mixing a culture solution (including 10% extracellular vesicle-free FBS) of a colorectal cancer cell line SW480 with a solution for inducing the precipitation of extracellular vesicles (8.4% polyethylene glycol 6000, 250 mM NaCl, 20 mM HEPES, and pH 7.2). Crude extracellular vesicles ($4 \times 10^{10}$ particles) harvested by centrifugation were loaded onto the Cu(II) ions-bound stationary phase column using HEPES buffer solution, washed with the same buffer solution of a 10 column volume. The eluates were fractionated into 1-ml fractions through processes including binding and washing processes with a concentration gradient using 0 to 500 mM imidazole/HEPES buffer solution for a 20 column volume. For all the eluted solutions during the HPLC process, chromatograms for each wavelength were secured by tracking absorbance at a wavelength of 260 nm and 280 nm, respectively.

Extracellular vesicle-specific signals derived from the colorectal cancer cell line and signals for CD9 antibodies were analyzed by applying eluates having the same volume to sandwich ELISA, while the concentration of extracellular vesicles was measured through a nanoparticle analysis.

Figure 20:
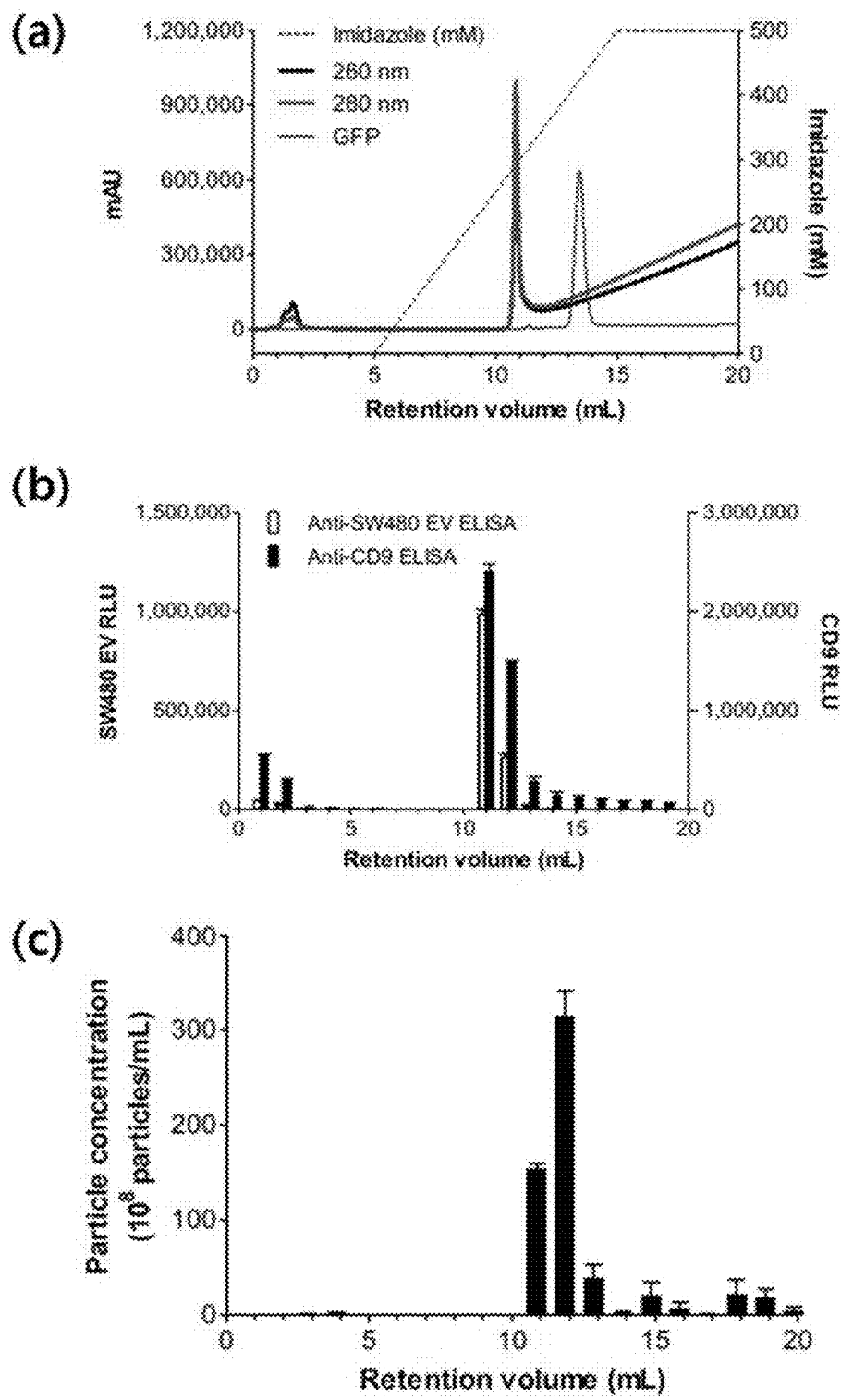
FIG. 20 is a result of confirming the result of isolating extracellular vesicles from a pre-treated cell culture solution according to an exemplary embodiment of the present invention by a chromatogram (a), sandwich ELISA (b), and nanoparticle analysis (c).

As a result, it was confirmed that at the same elution time as a 11-minute band on the chromatogram illustrated in FIG. 20(A), a signal for the extracellular vesicles derived from colorectal cancer cells and a strong signal for CD9 antibodies were detected (FIG. 20(B)), while through the nanoparticle analysis of the fractionated eluate, nanoparticle signals were detected at the same elution time as a 11-minute band on the chromatogram (FIG. 20(C)). Therefore, it was confirmed, by inducing the precipitation of the extracellular vesicles, that the extracellular vesicle solution obtained was bound to the Cu(II) ions-bound stationary phase, and thus were eluted and isolated by an imidazole concentration gradient.

Example 10. Isolation of Extracellular Vesicles from Culture Solution of Pre-Treated Colorectal Cancer Cell Line—Syringe Type Extracellular vesicles were isolated from a culture solution of the colorectal cancer cell line using the first method (see FIG. 1A) among the methods for isolating extracellular vesicles according to the present invention. Specifically, after 0.5 ml of 500 mM Cu(II) ions were bound to a column (1 ml) filled with a stationary phase (IDA-Sepharose) using a syringe system, non-bound residues were washed off with HEPES buffer solution of a 20 column volume.

Extracellular vesicles were precipitated by mixing a culture solution (including 10% extracellular vesicle-free FBS) of a colorectal cancer cell line SW480 with a solution for inducing precipitation of extracellular vesicles. Crude extracellular vesicles harvested by centrifugation were loaded onto the Cu(II) ions-bound stationary phase column using a syringe, washed with the same buffer solution of a 11 column volume, and then eluted with 1 ml (per time) of 50 mM imidazole/HEPEs buffer solution five times in total using a syringe.

Figure 21:
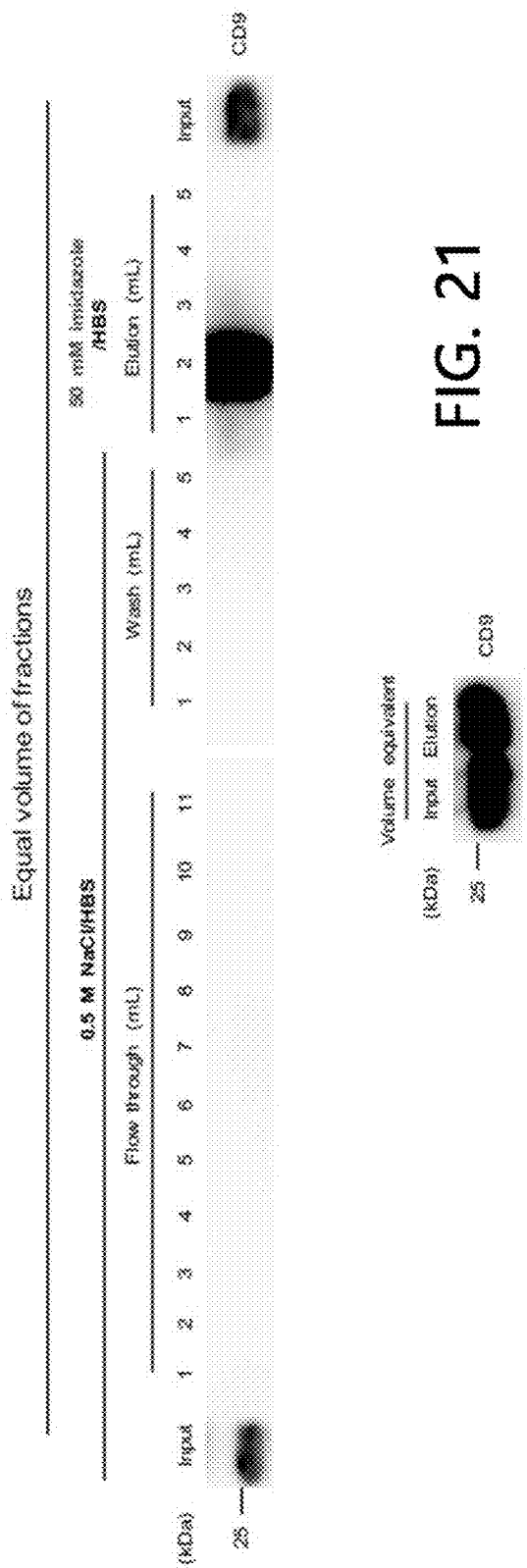
FIG. 21 is a result of confirming the fractionations of extracellular vesicles separated by a syringe type method from a pre-treated cell culture solution according to an exemplary embodiment of the present invention.

A Western blot analysis was performed on CD9, which is a typical marker for extracellular vesicles, from the non-bound eluate in the loading step, the eluate in the washing step, and the eluate in the imidazole step, respectively. The CD9 signal intensity was also analyzed for an equal amount of the pre-treated sample and the eluate in the imidazole step in order to confirm a respective yield. As a result, as illustrated in FIG. 21, most of the CD9 signals present in the sample confirmed that extracellular vesicles were bound to the Cu(II) ions-bound stationary phase and eluted from the 50 mM imidazole solution by the syringe type method. In addition, the intensity of the CD9 signals present in the sample was found significantly similar to that of the CD9 signals present in the eluate, confirming that extracellular vesicles could be isolated with high yield through the present technique.

Example 11. Isolation of Extracellular Vesicles from Pre-Treated Cell Culture Solution—Centrifugation Method Extracellular vesicles were isolated from a culture solution of the colorectal cancer cell line using the first method (see FIG. 1A) among the methods for isolating extracellular vesicles according to the present invention. Specifically, an empty column was filled with a stationary phase (IDA-Sepharose) using centrifugation (700×g, 1 minute) and 0.5 ml of 500 mM Cu(II) ions were loaded and bound to the column. HEPES buffer solution (1 ml each time) was then put into the column loaded with metal ions, and non-bound residues were washed off by centrifugation three times.

Extracellular vesicles were precipitated by mixing a culture solution (including 10% FBS excluding extracellular vesicles) of colorectal cancer cells with a solution for inducing precipitation of extracellular vesicles. Crude extracellular vesicles harvested by centrifugation were loaded onto a spun column filled with the Cu(II) ions stationary phase, followed by washing 1 ml (per each time) of extracellular vesicles by centrifugation using the same buffer solution three times in total. Subsequently, extracellular vesicles bound to the stationary phase were eluted using 0.5 ml (per each time) of 20 mM imidazole/HEPES buffer solution five times in total. In order to confirm the residual extracellular vesicles, the extracellular vesicles were finally washed with 100 mM imidazole.

Figure 22:
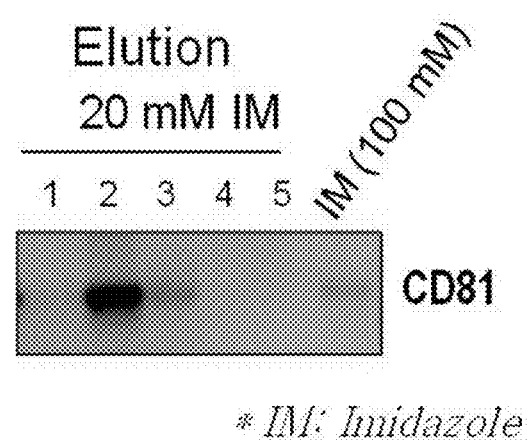
FIG. 22 is a result of isolating extracellular vesicles by a centrifugation method from a pre-treated cell culture solution according to an exemplary embodiment of the present invention.

SDS-electrophoresis was performed on each of the eluted fractions and the final wash, and signals for CD81, which is a typical marker for extracellular vesicles, were analyzed. As a result, as illustrated in FIG. 22, it was confirmed, by detecting strong CD81 signals in a second 20 mM imidazole elution fraction, that extracellular vesicles derived from colorectal cancer cells were bound to the Cu(II) ions-bound stationary phase even by centrifugation, and thus isolated under the 20 mM imidazole elution conditions.

Example 12. Isolation of Extracellular Vesicles from Pre-Treated Tissue Extract—Centrifugation Method Extracellular vesicles were isolated from the liver tissues of mice using the first method (see FIG. 1A) among the methods for isolating extracellular vesicles according to the present invention. Specifically, after an empty column was filled with a stationary phase (IDA-Sepharose) using centrifugation (700×g, 1 minute) and 0.5 ml of 500 mM Cu(II) ions were loaded and bound to the column. HEPES buffer solution (1 ml each time) was put into the column loaded with metal ions, and non-bound residues were washed by centrifugation three times in total.

In order to isolate extracellular vesicles in liver tissues, a liver tissue from which blood was removed through perfusion was extracted from an anesthetized mouse and washed with HEPES buffer solution. Then the tissue was cut into a size of 5 mm×5 mm, and again washed with HEPES buffer solution. After the washed mouse liver tissue was cultured at 37° C. for 30 minutes with an RPMI culture solution in which collagenase and DNase were mixed, the liver tissue was removed by centrifugation (500×g, 10 minutes). Floating materials were removed by centrifugation of the remaining liver tissue extract (2,000×g, 10 minutes, and twice in total).

Extracellular vesicles were precipitated by mixing the liver tissue extract from which the floating materials had been removed with a solution for inducing precipitation of extracellular vesicles, and crude extracellular vesicles were harvested by centrifugation. A fraction containing extracellular vesicles and having a molecular weight of 500 kDa or more was obtained from the harvested crude extracellular vesicle solution using Sephacryl S500 molecular size chromatography, and loaded onto a spun column filled with the Cu(II) ions-bound stationary phase, followed by centrifugation to obtain a flow through. The column was washed with 0.5 ml (per each time) of HEPES buffer solution three times in total. Next, in order to isolate the bound extracellular vesicles from the stationary phase, 0.5 ml (per each time) of 50 mM ethylenediaminetetraacetate (EDTA)/HEPES buffer solution was loaded onto the washed column three times in total, and an eluate was harvested by centrifugation.

Figure 23:
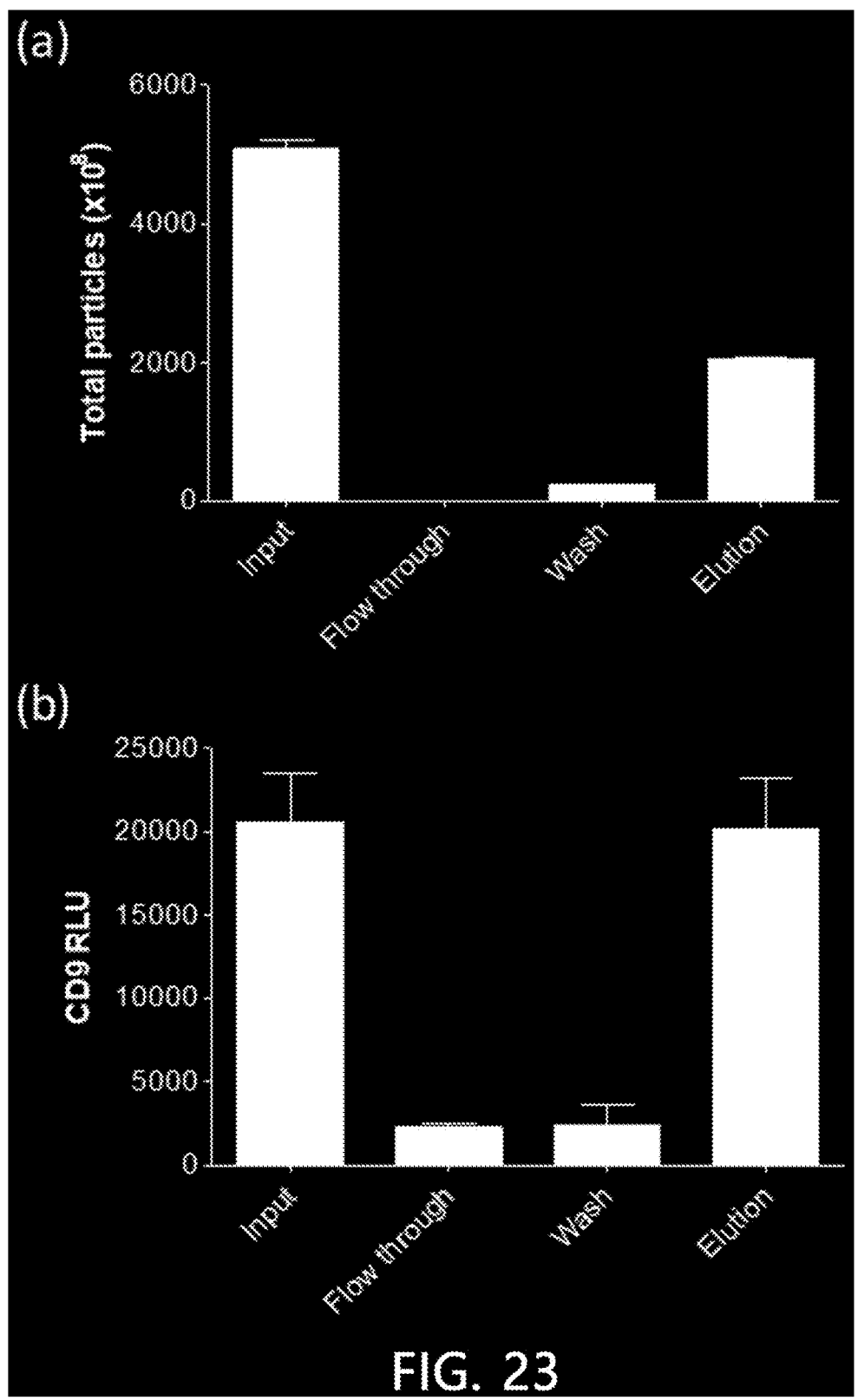
FIG. 23 is a result of confirming the result of isolating extracellular vesicles by a centrifugation method from a pre-treated tissue extraction solution according to an exemplary embodiment of the present invention via nanoparticle analysis (a) and chemiluminescence signal analysis (b).

For a result analysis, a nanoparticle analysis was performed on the sample loaded onto the column, the flow through, and the EDTA eluate. They were adsorbed onto a microplate, followed by reacting with CD9, which is a typical marker for extracellular vesicles, and chemiluminescence signals were analyzed by reacting an antibody against an anti-rat antibody bound to horseradish peroxidase. As a result, as illustrated in FIG. 23, it was observed that no nanoparticle signals were detected in the flow through and washing process, a high nanoparticle signal was detected in the EDTA eluate (FIG. 23(A)), most of the substances exhibiting a CD9 positive reaction in the sample were bound to the stationary phase and eluted by EDTA, but CD9 signals were very low in the flow through (FIG. 23(B)). Therefore, it was confirmed that extracellular vesicles can be isolated in high yield from a liver tissue extract.

Example 13. Isolation of Extracellular Vesicles from Pre-Treated Cancer Tissue Extract—Centrifugation Method Extracellular vesicles were isolated from cancer tissues of mice using the first method (see FIG. 1A) among the methods for isolating extracellular vesicles according to the present invention. Specifically, after an empty column was filled with a stationary phase (IDA-Sepharose) using centrifugation (700×g, 1 minute) and 0.5 ml of 500 mM Cu(II) ions were loaded and bound to the column. HEPES buffer solution (1 ml per each time) was put into the column loaded with metal ions, and non-bound residues were washed off by centrifugation three times in total.

After a cancer tissue was cultured by subcutaneously injecting CT26 cancer cells into a mouse, the cancer tissue was extracted from the anaesthetized mouse. After the cancer tissue was washed with HEPES buffer solution, the tissue was cut into a size of 5 mm×5 mm, and washed again with HEPES buffer solution. After the washed cancer tissue was cultured at 37° C. for 30 minutes with an RPMI culture solution in which collagenase and DNase were mixed, the cancer tissue was removed by centrifugation (500×g, 10 minutes). Floating materials were removed by centrifugation of the remaining cancer tissue extract again (2,000×g, 10 minutes, and twice in total).

Extracellular vesicles were precipitated by mixing the cancer tissue extract from which the floating material had been removed with a solution for inducing precipitation of extracellular vesicles, and crude extracellular vesicles were harvested by centrifugation. A fraction containing extracellular vesicles and having a molecular weight of 500 kDa or more was obtained from the harvested crude extracellular vesicle solution using Sephacryl S500 molecular size chromatography, and loaded onto a spun column filled with the Cu(II) ions-bound stationary phase, followed by harvesting a flow through by centrifugation. The column was washed with 0.5 ml (per each time) of HEPES buffer solution three times in total. Next, in order to isolate the bound extracellular vesicles from the stationary phase, 0.5 ml (per each time) of 50 mM EDTA/HEPES buffer solution was loaded onto the washed column three times in total, and an eluate was harvested by centrifugation.

Figure 24:
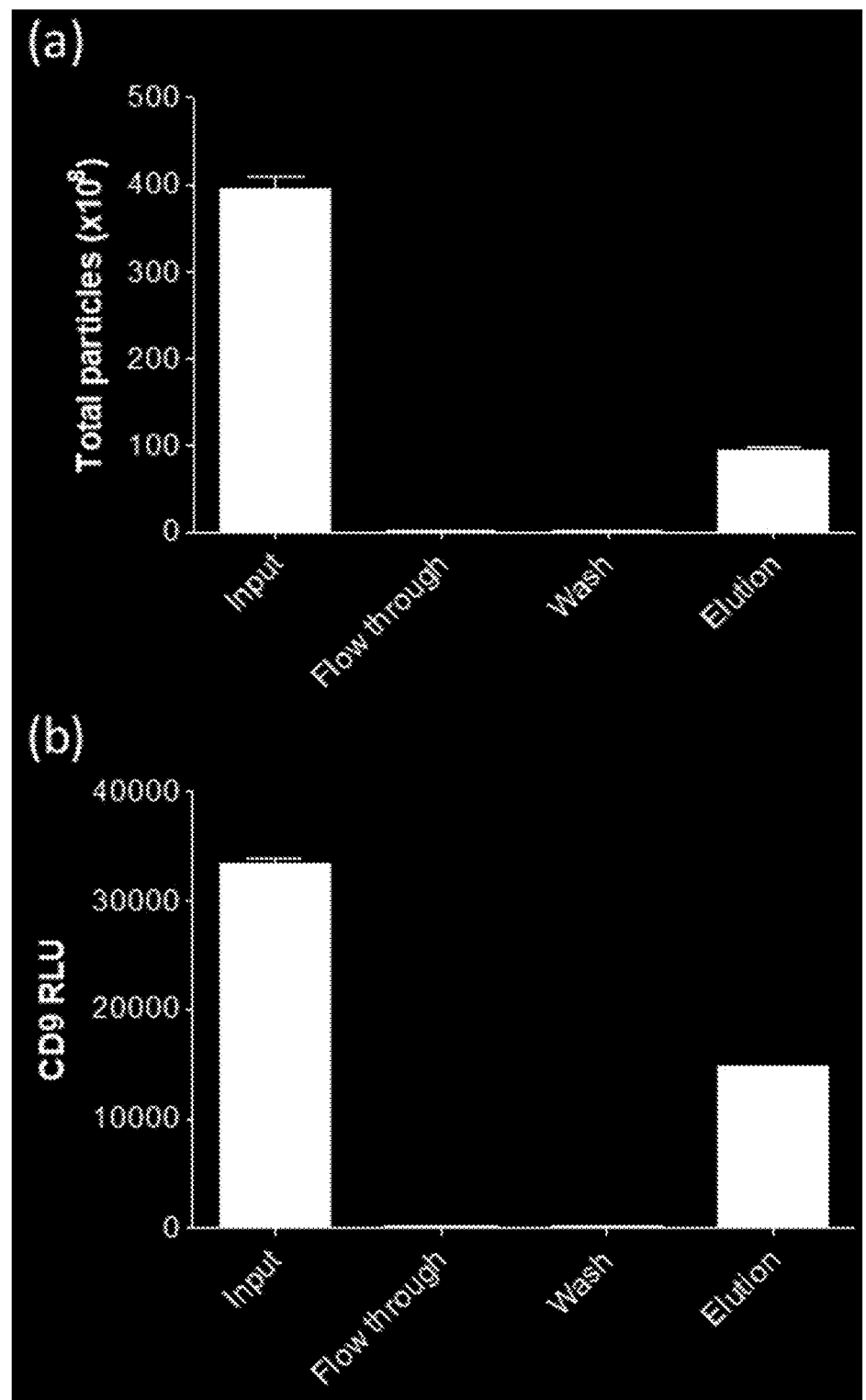
FIG. 24 is a result of confirming the result of isolating extracellular vesicles by a centrifugation method from a pre-treated cancer tissue extraction solution according to an exemplary embodiment of the present invention via nanoparticle analysis (a) and chemiluminescence signal analysis (b).

A nanoparticle analysis was performed on the sample loaded onto the column, the flow through, and the EDTA eluate. They were adsorbed onto a microplate, followed by reacting with CD9, which is a typical marker for extracellular vesicles, and analyzing chemiluminescence signals by reacting an antibody against an anti-rat antibody bound to horseradish peroxidase. As a result, as illustrated in FIG. 24, it was observed that no nanoparticle signals were detected in the flow through and washing process, a high nanoparticle signal was detected in the EDTA eluate (FIG. 24(A)), most of the substances exhibiting a CD9 positive reaction in the sample were bound to the stationary phase and eluted by EDTA which is a metal chelate, but no CD9 signal was detected in the flow through (FIG. 24(B)). Therefore, it was confirmed that extracellular vesicles can be isolated from a cancer tissue extract by the present method.

Example 14. Isolation of Extracellular Vesicles from Pretreated Urine—Pump Type

Extracellular vesicles were isolated from a human urine sample using the first method (see FIG. 1A) among the methods for isolating extracellular vesicles according to the present invention. Specifically, after 0.5 ml of 500 mM Cu(II) ions were bound to a column (1 ml) filled with a stationary phase (IDA-Sepharose) using an HPLC system, non-bound residues were washed off with HEPES buffer solution of a 20 column volume.

After human urine was collected and filtered with a 0.45 mm filter, extracellular vesicles were precipitated by mixing the human urine with a solution for inducing extracellular vesicles. A fraction containing extracellular vesicles and having a molecular weight of 500 kDa or more was obtained from crude extracellular vesicles harvested by centrifugation using Sephacryl S500 molecular size chromatography and loaded onto a column filled with the Cu(II) ions-bound stationary phase. After washing with the same buffer solution of a 5 column volume, the eluate was fractionated into 1-ml fractions through processes comprising binding and washing processes with a concentration gradient using 0 to 500 mM imidazole/HEPES buffer solution for a 20 column volume. For all the solution eluted during the HPLC process, a chromatogram for each wavelength was secured by tracking absorbance at a wavelength of 260 nm and 280 nm, respectively. Eluted fractions having the same volume were subjected to a nanoparticle analysis and adsorbed onto a microplate, and then a monoclonal anti-CD9 antibody against a typical marker CD9 for extracellular vesicles were reacted, and then chemiluminescence was measured by additionally culturing an antibody against an anti-mouse antibody bound to horseradish peroxidase.

Figure 25:
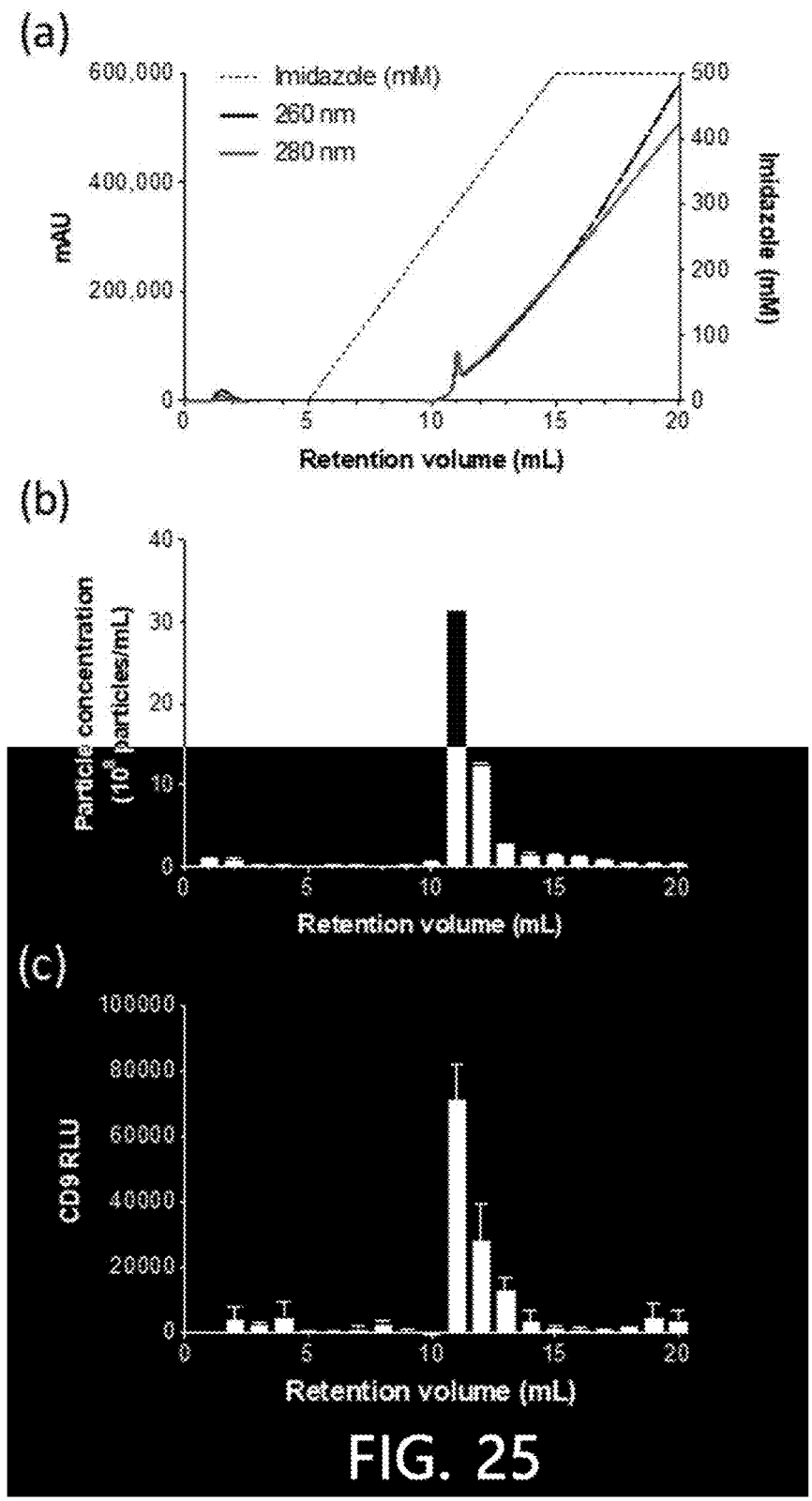
FIG. 25 is a result of confirming the result of isolating extracellular vesicles from pre-treated urine according to an exemplary embodiment of the present invention by a chromatogram (a), nanoparticle analysis (b), and ELISA (c).

As illustrated in FIG. 25, it was found that a nanoparticle signal with a high strength (FIG. 25(B)) was detected at the same elution time as a 11 minute band on the chromatogram (FIG. 25(A)), and a strong CD9 signal (FIG. 25(C)) was detected at the same elution time as the 11 minute band on the chromatogram through a Western blot analysis for CD9 antibodies. Therefore, it was confirmed that extracellular vesicles in urine can be bound using a Cu(II) ions-bound stationary phase, followed by elution and isolation using imidazole.

Example 15. Isolation of Bacteria-Derived Extracellular Vesicles from Pre-Treated E. coli Culture Solution—Centrifugation Method Extracellular vesicles were isolated from an E. coli culture solution using the first method (see FIG. 1A) among the methods for isolating extracellular vesicles according to the present invention. Specifically, after an empty column was filled with a stationary phase (IDA-Sepharose) using centrifugation (700×g, 1 minute) and 0.5 ml of 500 mM Cu(II) ions were loaded and bound to the column, HEPES buffer solution (1 ml each time) was put into the column loaded with metal ions, and non-bound residues were washed off by centrifugation three times.

After an E. coli culture solution (E. coli C4 culture medium) was filtered with a 0.45 mm filter, extracellular vesicles derived from E. coli were precipitated by mixing the E. coli culture solution with a solution for inducing the precipitation of extracellular vesicles. A fraction containing extracellular vesicles and having a molecular weight of 500 kDa or more was obtained from crude extracellular vesicles harvested by centrifugation using Sephacryl S500 molecular size chromatography and loaded onto a column filled with the Cu(II) ions-bound stationary phase.

A flow through was harvested by centrifugation, and the column was washed with 0.5 ml (per each time) of HEPES buffer solution three times in total. Next, in order to isolate the bound E. coli-derived extracellular vesicles from the stationary phase, 0.5 ml (per each time) of 50 mM EDTA/HEPES buffer solution was loaded onto the washed column three times in total, and an eluate was harvested by centrifugation.

After the sample loaded onto the column, the flow through, and the EDTA eluate were adsorbed onto a microplate, followed by adding and reacting with polyclonal anti-E. coli derived extracellular vesicle antibodies. Subsequently, chemiluminescence was measured by additionally culturing an antibody against an anti-rabbit antibody bound to horseradish peroxidase.

Figure 26:
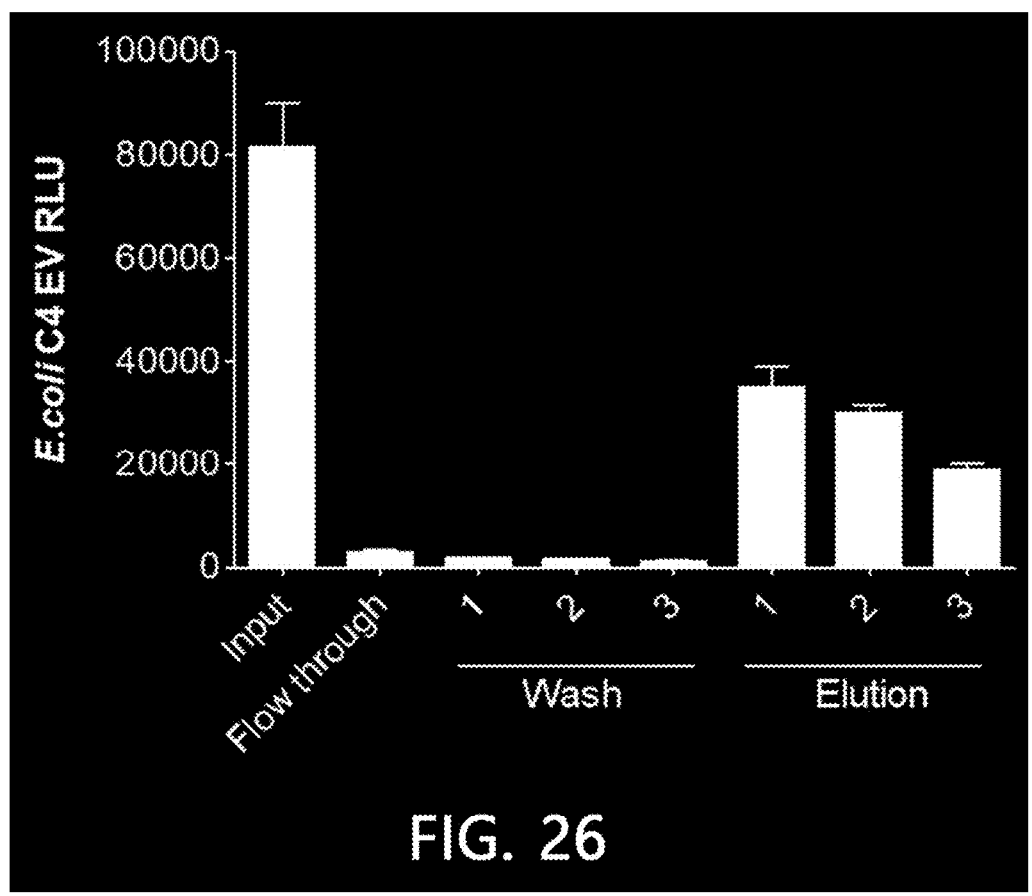
FIG. 26 is a result of confirming the result of isolating extracellular vesicles from a pre-treated *E. coli* culture solution according to an exemplary embodiment of the present invention by ELISA.

As a result, as illustrated in FIG. 26, most of the substances reacting with a polyclonal anti-E. coli derived extracellular vesicle antibody in the sample were bound to the Cu(II) ions-bound stationary phase, and were eluted by EDTA which is a metal chelate, while no signal for the polyclonal anti-E. coli-derived extracellular vesicle antibody was detected in the flow through. Therefore, it was confirmed that extracellular vesicles derived from E. coli can be isolated with high yield by the method according to the present invention.

Example 16. Isolation of Yeast-Derived Extracellular Vesicles from Pre-Treated Beer—Centrifugation Method Extracellular vesicles were isolated from beer using the first method (see FIG. 1A) among the methods for isolating extracellular vesicles according to the present invention. Specifically, after an empty column was filled with a stationary phase (IDA-Sepharose) using centrifugation (700×g, 1 minute) and 0.5 ml of 500 mM Cu(II) ions were loaded and bound to the column, HEPES buffer solution (1 ml each time) was put into the column loaded with metal ions, and non-bound residues were washed off by centrifugation three times.

After the beer was filtered with a 0.45 mm filter, extracellular vesicles were precipitated by mixing the beer with a solution for inducing the precipitation of extracellular vesicles. A fraction containing extracellular vesicles and having a molecular weight of 500 kDa or more was obtained from crude extracellular vesicles harvested by centrifugation using Sephacryl S500 molecular size chromatography and loaded onto a column filled with the Cu(II) ions-bound stationary phase.

A flow through was harvested by centrifugation, and the column was washed with 0.5 ml (per each time) of HEPES buffer solution three times in total. Next, in order to isolate the bound extracellular vesicles from the stationary phase, 0.5 ml (per each time) of 50 mM EDTA/HEPES buffer solution was loaded onto the washed column three times in total, and then an eluate was harvested by centrifugation.

After the sample loaded onto the column, the flow through, and the EDTA eluate were adsorbed onto a microplate, followed by adding and reacting with a polyclonal anti-yeast-derived extracellular vesicle antibody. Subsequently, chemiluminescence was measured by additionally culturing an antibody against an anti-rabbit antibody bound to horseradish peroxidase.

Figure 27:
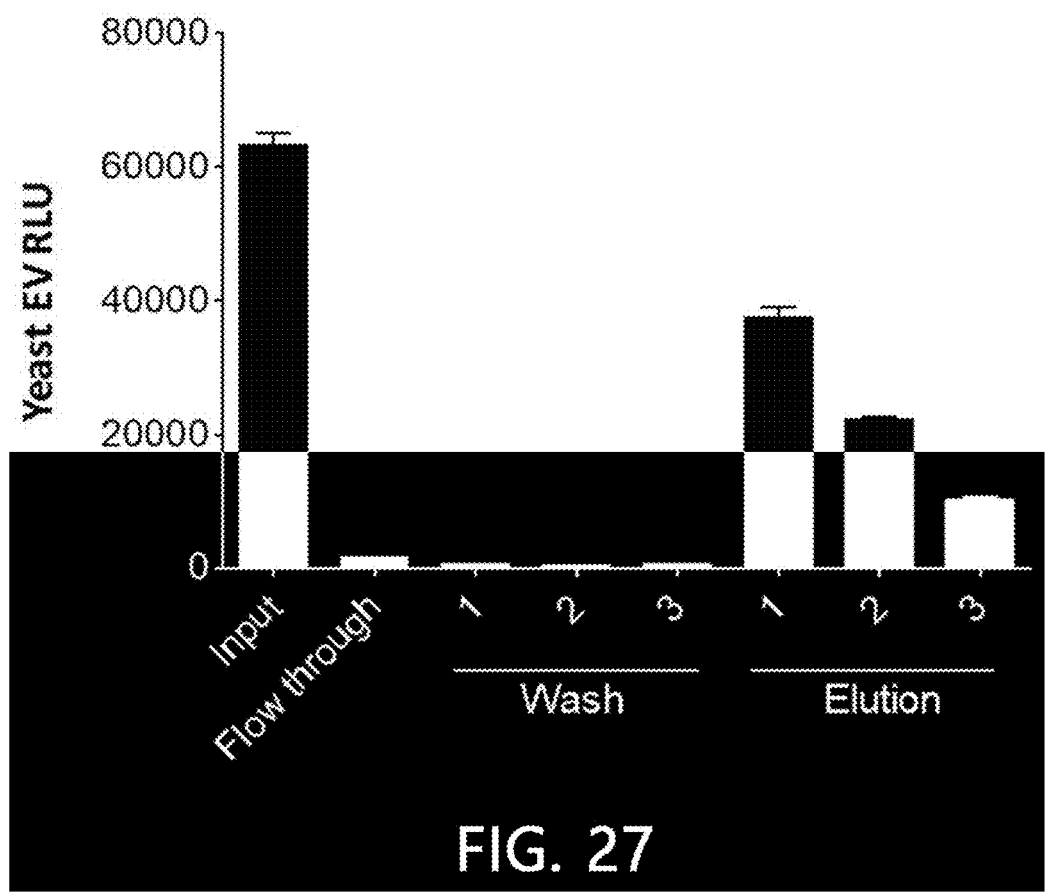
FIG. 27 is a result of confirming the result of isolating extracellular vesicles from pre-treated beer according to an exemplary embodiment of the present invention by ELISA.

As a result, as illustrated in FIG. 27, most of the substances reacting with a polyclonal anti-yeast-derived extracellular vesicle antibody in the sample were bound to the Cu(II) ions-bound stationary phase, and were eluted by EDTA which is a metal chelate, while no signal for the polyclonal anti-yeast-derived extracellular vesicle antibody was detected in the flow through. Therefore, it was confirmed that extracellular vesicles derived from yeast in beer can be isolated with high yield by the method according to the present invention.

Figure 1B:
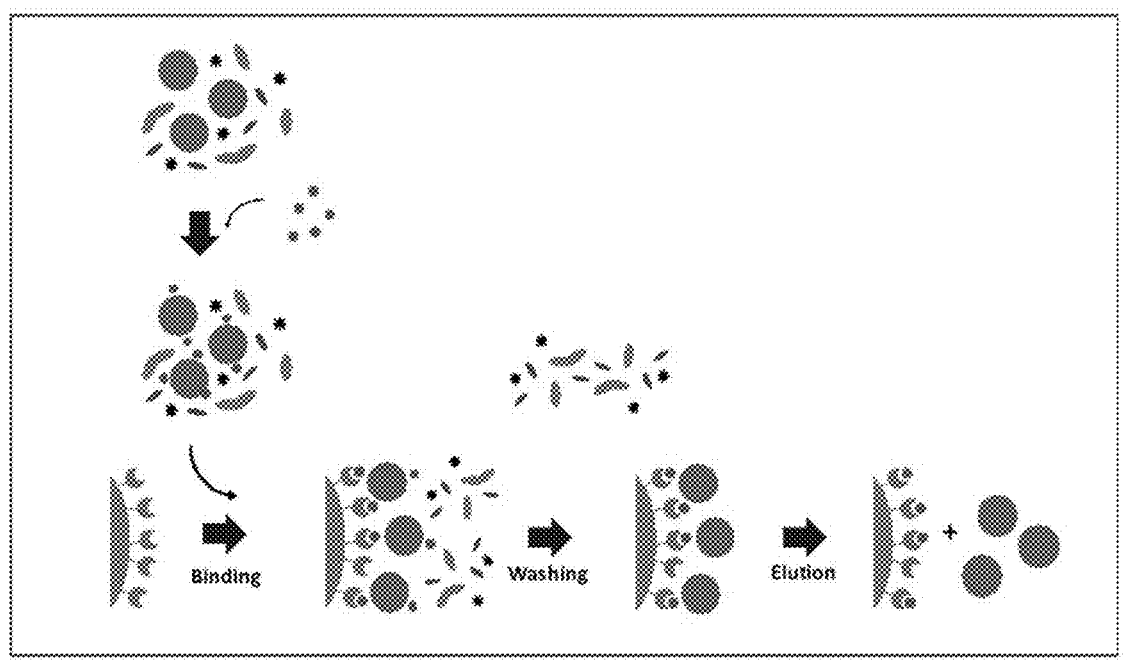
Figure 1B:
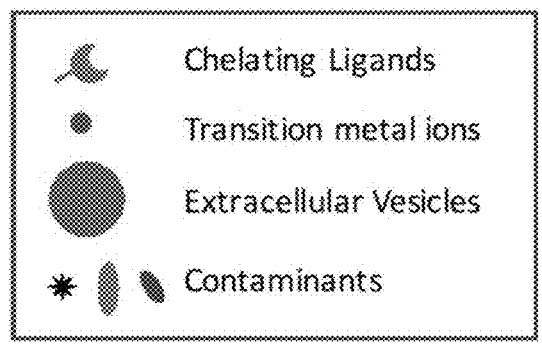

Example 17. Isolation of Extracellular Vesicles from Pre-Treated Cell Culture Solution Extracellular vesicles were isolated from a culture solution of colorectal cancer cells using the second method (see FIG. 1B) among the methods for isolating extracellular vesicles according to the present invention. Specifically, extracellular vesicles were precipitated by mixing the culture solution of colorectal cancer cells with a solution for inducing the precipitation of extracellular vesicles, and Cu(II) ions at a final concentration of 5 mM were added to a crude extracellular vesicle solution harvested by centrifugation A spun column was filled with 1 ml of a stationary phase (IDA-Sepharose), followed by washing with 1 ml (per each time) of water three times in total by centrifugation (700×g, 1 minute). After a Cu(II) ions-added sample was loaded onto the washed stationary phase and un-bound solution was harvested by centrifugation, the column was washed with 1 each ml of HEPES buffer solution three times in total.

Figure 28:
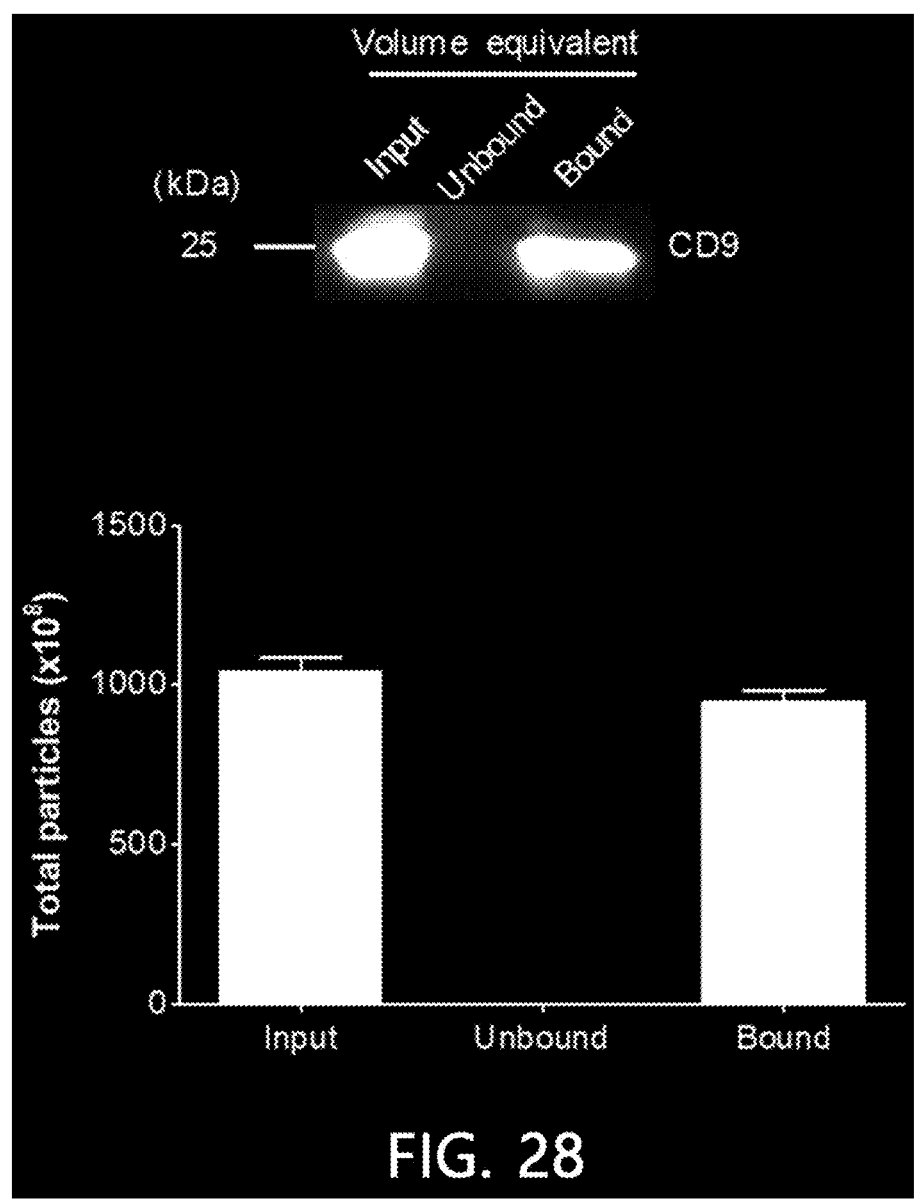
FIG. 28 is a result of confirming the result of isolating extracellular vesicles from a pre-treated cell culture solution using the method of FIG. 1B according to an exemplary embodiment of the present invention by a Western blot and nanoparticle analysis.

In order to elute the extracellular vesicles bound to the stationary phase, extracellular vesicles were eluted by adding 1 ml of 50 mM EDTA/HEPES buffer solution to the washed column, and performing centrifugation under the same conditions as those described above. A nanoparticle analysis was performed on the sample loaded onto the column, the flow through, and the EDTA eluate, and a Western blot analysis was performed on CD9 which is a typical marker for extracellular vesicles. As a result, as illustrated in FIG. 28, 90% or more of the nanoparticle signals were bound to the stationary phase, and eluted by EDTA which is a metal chelate. Further, there was no nanoparticle signal in the flow through, confirming that extracellular vesicles were isolated with high yield using the method of the present invention. Moreover, even in the Western blot analysis of CD9 which is a typical marker for extracellular vesicles, it was confirmed that 90% or more of the CD9 signals in the sample were bound to the stationary phase, and then eluted by EDTA in the same manner as in the nanoparticle analysis.

Figure 1C:
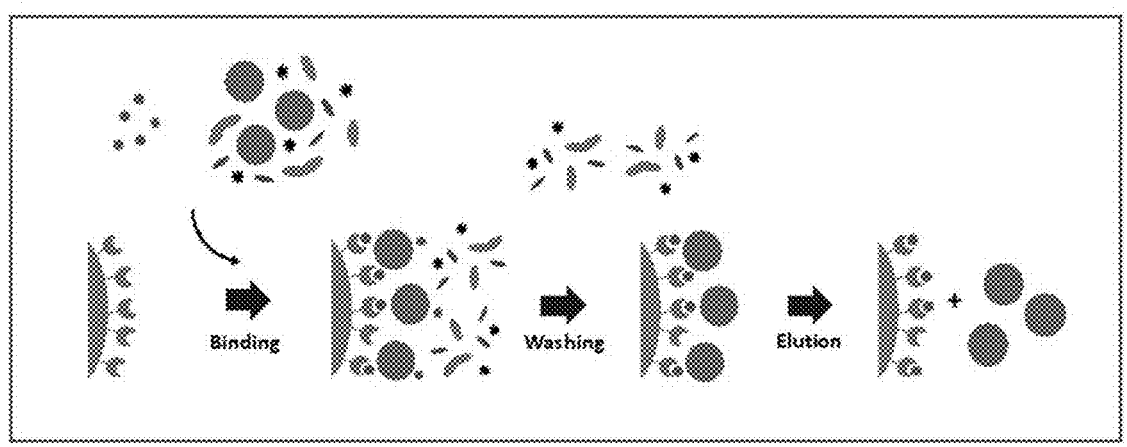
Figure 1C:
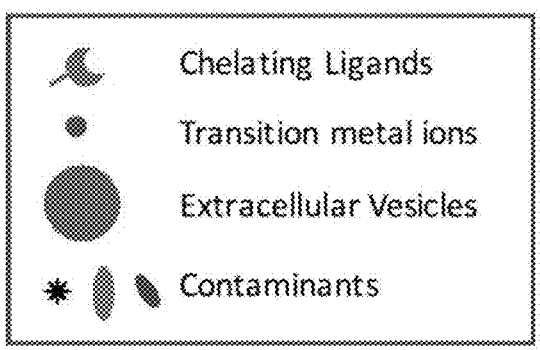

Example 18. Isolation of Extracellular Vesicles from Pre-Treated Cell Culture Solution Extracellular vesicles were isolated from a culture solution of colorectal cancer cells using the third method (see FIG. 1C) among the methods for isolating extracellular vesicles according to the present invention. Specifically, extracellular vesicles were precipitated by mixing the culture solution of colorectal cancer cells with a solution for inducing the precipitation of extracellular vesicles, and crude extracellular vesicles were harvested by centrifugation. A suspension containing a solution of the harvested crude extracellular vesicles, 5 mM Cu(II) ions, and 1 ml of a stationary phase (IDA-Sepharose) washed with water was cultured at 25° C. for 30 minutes. The suspension was loaded onto a spun column, a un-bound solution was harvested by centrifugation (700×g, 1 minute), and then the column was washed with 1 each ml of HEPES buffer solution by centrifugation three times in total.

Figure 29:
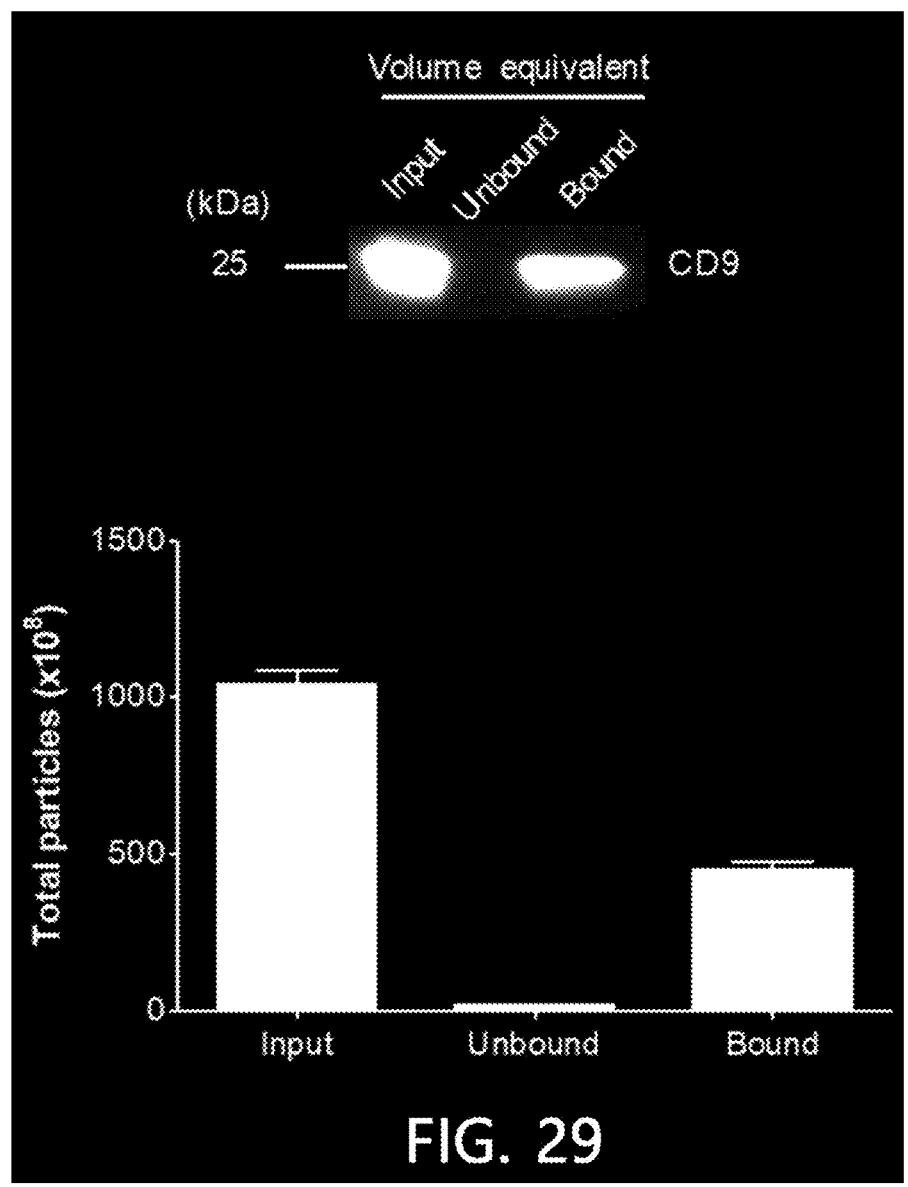
FIG. 29 is a result of confirming the result of isolating extracellular vesicles from a pre-treated cell culture solution using the method of FIG. 1C according to an exemplary embodiment of the present invention by a Western blot and nanoparticle analysis.

In order to elute the extracellular vesicles bound to the stationary phase, extracellular vesicles were eluted by adding 1 ml of 50 mM EDTA/HEPES buffer solution to the washed column, and performing centrifugation under the same conditions as those described above. A nanoparticle analysis was performed on the sample loaded onto the column, the flow through, and the EDTA eluate, and a Western blot analysis was performed on CD9 which is a typical marker for extracellular vesicles. As a result, as illustrated in FIG. 29, although most of the nanoparticle signals and the substances exhibiting a CD9 positive reaction in the sample were bound to the stationary phase and eluted by EDTA which is a metal chelate, there were no nanoparticle signals and CD signals in the flow through. Thus, it was confirmed that the extracellular vesicles in the sample can be isolated with high yield using the method of the present invention.

The invention claimed is:

1. A method for isolating extracellular vesicles, the method comprising steps of:
   (a) immobilizing chelate ligands onto a stationary phase;
   (b) adding metals to the stationary phase onto which the chelate ligands are immobilized, and immobilizing the metals onto the chelate ligands;
   (c) washing off metal residues which are not immobilized onto the chelate ligands;
   (d) injecting samples comprising extracellular vesicles into the washed stationary phase and binding the extracellular vesicles to the metals which are immobilized onto the chelate ligands;
   (e) washing off sample residues to which the metals are not bound in the stationary phase; and
   (f) eluting metal-bound extracellular vesicles from the stationary phase,
   wherein the metal is one or more selected from the group consisting of scandium (Sc), yttrium (Y), titanium (Ti), zirconium (Zr), hafnium (Hf), rutherfordium (Rf), vanadium (V), niobium (Nb), tantalum (Ta), dubnium (Db), chromium (Cr), molybdenum (Mo), tungsten (W), seaborgium (Sg), manganese (Mn), technetium (Tc), rhenium (Re), bohrium (Bh), iron (Fe), ruthenium (Ru), osmium (Os), hassium (Hs), cobalt (Co), rhodium (Rh), iridium (Ir), meitnerium (Mt), nickel (Ni), palladium (Pd), platinum (Pt), darmstadtium (Ds), copper (Cu), silver (Ag), gold (Au), roentgenium (Rg), zinc (Zn), cadmium (Cd), mercury (Hg), copernicium (Cn), aluminum (Al), and gallium (Ga).

2. The method of claim 1, wherein the stationary phase is one or more selected from the group consisting of an agarose bead, a sepharose bead, a magnetic bead, a gold nanoparticle, an iron oxide nanoparticle, a nylon membrane, a nitrocellulose membrane, a PVDF membrane, paper, plastic, sand, glass, and a metal sensor chip.

3. The method of claim 1, wherein the chelate ligand is one or more selected from the group consisting of iminodiacetic acid (IDA), nitrilotriacetic acid (NTA), tris-(carboxymethyl)ethylenediamine (TED), ethylenediamine, ethylendiamine tetraacetate (EDTA), alkylenediamine triacetic acid, diethylenetriaminepentaacetic acid (DTPA), ethylene glycol-bis(β-aminoethyl ether)-N,N,N',N'-tetraacetic acid (EGTA), phosphoserine, and 1,4,7-triazocyclononane (TACN).

4. The method of claim 1, wherein the sample is one or more selected from the group consisting of a mammal cell culture medium, a bacterial cell culture medium, a yeast culture medium, a tissue extract, a cancer tissue, serum, blood plasma, saliva, tears, sweat, urine, feces, cerebrospinal fluid (CSF), ascites, amniotic fluid, semen, milk, dust, fresh water, seawater, soil, and fermented food.

5. The method of claim 1, further comprising a step of pre-treating the samples prior to the addition of the samples to the stationary phase and/or a step of post-treating an eluate obtained after eluting the metal-bound extracellular vesicles.

6. The method of claim 5, wherein the step of pre-treating the samples is conducted by one or more methods selected from the group consisting of centrifugation, ultracentrifugation, filtration, ultrafiltration, sonication, density gradient ultracentrifugation, size-exclusion chromatography, ion exchange chromatography, affinity chromatography, polymer-based precipitation, and organic solvent precipitation; and the step of post-treating an eluate is conducted by one or more methods selected from the group consisting of centrifugation, ultracentrifugation, filtration, ultrafiltration, sonication, density gradient ultracentrifugation, size-exclusion chromatography, ion exchange chromatography, affinity chromatography, polymer-based precipitation, and organic solvent precipitation.

7. A method for isolating extracellular vesicles, the method comprising steps of:
(a) immobilizing chelate ligands onto a stationary phase;
(b) mixing metals with samples comprising extracellular vesicles, thereby binding the metals to the extracellular vesicles;
(c) adding the obtained metal and sample mixture to the stationary phase onto which the chelate ligands are immobilized, and immobilizing the extracellular vesicle-bound metals onto the chelate ligands;
(d) washing off residues which are not immobilized onto the stationary phase; and
(e) eluting metal-bound extracellular vesicles from the stationary phase,
wherein the metal is one or more selected from the group consisting of scandium (Sc), yttrium (Y), titanium (Ti), zirconium (Zr), hafnium (Hf), rutherfordium (Rf), vanadium (V), niobium (Nb), tantalum (Ta), dubnium (Db), chromium (Cr), molybdenum (Mo), tungsten (W), seaborgium (Sg), manganese (Mn), technetium (Tc), rhenium (Re), bohrium (Bh), iron (Fe), ruthenium (Ru), osmium (Os), hassium (Hs), cobalt (Co), rhodium (Rh), iridium (Ir), meitnerium (Mt), nickel (Ni), palladium (Pd), platinum (Pt), darmstadtium (Ds), copper (Cu), silver (Ag), gold (Au), roentgenium (Rg), zinc (Zn), cadmium (Cd), mercury (Hg), copernicium (Cn), aluminum (Al), and gallium (Ga).

8. The method of claim 7, wherein the stationary phase is one or more selected from the group consisting of an agarose bead, a sepharose bead, a magnetic bead, a gold nanoparticle, an iron oxide nanoparticle, a nylon membrane, a nitrocellulose membrane, a PVDF membrane, paper, plastic, sand, glass, and a metal sensor chip.

9. The method of claim 7, wherein the chelate ligand is one or more selected from the group consisting of iminodiacetic acid (IDA), nitrilotriacetic acid (NTA), tris-(carboxymethyl)ethylenediamine (TED), ethylenediamine, ethylendiamine tetraacetate (EDTA), alkylenediamine triacetic acid, diethylenetriaminepentaacetic acid (DTPA), ethylene glycol-bis(β-aminoethyl ether)-N,N,N',N'-tetraacetic acid (EGTA), phosphoserine, and 1,4,7-triazocyclononane (TACN).

10. The method of claim 7, wherein the sample is one or more selected from the group consisting of a mammal cell culture medium, a bacterial cell culture medium, a yeast culture medium, a tissue extract, a cancer tissue, serum, blood plasma, saliva, tears, sweat, urine, feces, cerebrospinal fluid (CSF), ascites, amniotic fluid, semen, milk, dust, fresh water, seawater, soil, and fermented food.

11. The method of claim 7, further comprising a step of pre-treating the samples prior to the addition of the samples to the stationary phase and/or a step of post-treating an eluate obtained after eluting the metal-bound extracellular vesicles.

12. The method of claim 11, wherein the step of pre-treating the samples is conducted by one or more methods selected from the group consisting of centrifugation, ultracentrifugation, filtration, ultrafiltration, sonication, density gradient ultracentrifugation, size-exclusion chromatography, ion exchange chromatography, affinity chromatography, polymer-based precipitation, and organic solvent precipitation; and the step of post-treating an eluate is conducted by one or more methods selected from the group consisting of centrifugation, ultracentrifugation, filtration, ultrafiltration, sonication, density gradient ultracentrifugation, size-exclusion chromatography, ion exchange chromatography, affinity chromatography, polymer-based precipitation, and organic solvent precipitation.

13. A method for isolating extracellular vesicles, the method comprising steps of:
(a) immobilizing chelate ligands onto a stationary phase;
(b) adding metals and samples comprising extracellular vesicles to the stationary phase onto which the chelate ligands are immobilized;
(c) immobilizing the metals onto the chelate ligands, and binding the extracellular vesicles to the metals;
(d) washing off residues which are not immobilized onto the stationary phase; and
(e) eluting metal-bound extracellular vesicles from the stationary phase,
wherein the metal is one or more selected from the group consisting of scandium (Sc), yttrium (Y), titanium (Ti), zirconium (Zr), hafnium (Hf), rutherfordium (Rf), vanadium (V), niobium (Nb), tantalum (Ta), dubnium (Db), chromium (Cr), molybdenum (Mo), tungsten (W), seaborgium (Sg), manganese (Mn), technetium (Tc), rhenium (Re), bohrium (Bh), iron (Fe), ruthenium (Ru), osmium (Os), hassium (Hs), cobalt (Co), rhodium (Rh), iridium (Ir), meitnerium (Mt), nickel (Ni), palladium (Pd), platinum (Pt), darmstadtium (Ds), copper (Cu), silver (Ag), gold (Au), roentgenium (Rg), zinc (Zn), cadmium (Cd), mercury (Hg), copernicium (Cn), aluminum (Al), and gallium (Ga).

14. The method of claim 13, wherein the stationary phase is one or more selected from the group consisting of an agarose bead, a sepharose bead, a magnetic bead, a gold nanoparticle, an iron oxide nanoparticle, a nylon membrane, a nitrocellulose membrane, a PVDF membrane, paper, plastic, sand, glass, and a metal sensor chip.

15. The method of claim 13, wherein the chelate ligand is one or more selected from the group consisting of iminodiacetic acid (IDA), nitrilotriacetic acid (NTA), tris-(carboxymethyl)ethylenediamine (TED), ethylenediamine, ethylendiamine tetraacetate (EDTA), alkylenediamine triacetic acid, diethylenetriaminepentaacetic acid (DTPA), ethylene glycol-bis(β-aminoethyl ether)-N,N,N',N'-tetraacetic acid (EGTA), phosphoserine, and 1,4,7-triazocyclononane (TACN).

16. The method of claim 13, wherein the sample is one or more selected from the group consisting of a mammal cell culture medium, a bacterial cell culture medium, a yeast culture medium, a tissue extract, a cancer tissue, serum, blood plasma, saliva, tears, sweat, urine, feces, cerebrospinal fluid (CSF), ascites, amniotic fluid, semen, milk, dust, fresh water, seawater, soil, and fermented food.

17. The method of claim 13, further comprising a step of pre-treating the samples prior to the addition of the samples to the stationary phase and/or a step of post-treating an eluate obtained after eluting the metal-bound extracellular vesicles.

18. The method of claim 17, wherein the step of pre-treating the samples is conducted by one or more methods selected from the group consisting of centrifugation, ultracentrifugation, filtration, ultrafiltration, sonication, density gradient ultracentrifugation, size-exclusion chromatography, ion exchange chromatography, affinity chromatography, polymer-based precipitation, and organic solvent precipitation; and the step of post-treating an eluate is conducted by one or more methods selected from the group consisting of centrifugation, ultracentrifugation, filtration, ultrafiltration, sonication, density gradient ultracentrifugation, size-exclusion chromatography, ion exchange chromatography, affinity chromatography, polymer-based precipitation, and organic solvent precipitation.

19. The method of claim 13, wherein the metals and the samples comprising extracellular vesicles are obtained by mixing metals with samples comprising extracellular vesicles, thereby binding the metals to the extracellular vesicles.

* * * * *